(12) United States Patent
Lo et al.

(10) Patent No.: US 9,074,978 B2
(45) Date of Patent: Jul. 7, 2015

(54) OPTICAL SPACE-TIME CODING TECHNIQUE IN MICROFLUIDIC DEVICES

(75) Inventors: Yu-Hwa Lo, San Diego, CA (US); Tsung-Feng Wu, La Jolla, CA (US); Zhe Mei, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/548,160

(22) Filed: Jul. 12, 2012

(65) Prior Publication Data

US 2013/0016335 A1 Jan. 17, 2013

Related U.S. Application Data

(60) Provisional application No. 61/507,068, filed on Jul. 12, 2011.

(51) Int. Cl.
| | |
|---|---|
| *G01P 3/36* | (2006.01) |
| *G01N 15/14* | (2006.01) |
| *G01P 5/00* | (2006.01) |
| *G01P 5/20* | (2006.01) |
| *G01P 5/26* | (2006.01) |
| *G01N 15/10* | (2006.01) |

(52) U.S. Cl.
CPC ............ *G01N 15/1459* (2013.01); *G01P 5/001* (2013.01); *G01P 5/20* (2013.01); *G01P 5/26* (2013.01); *G01N 2015/1006* (2013.01); *G01N 2015/1486* (2013.01); *G01N 2015/1493* (2013.01); *G01N 15/1484* (2013.01)

(58) Field of Classification Search
CPC ............ G01P 3/36; G01P 5/26; G01P 3/366; G01S 17/50; G01S 17/58
USPC .......................................................... 356/28
See application file for complete search history.

(56) References Cited

U.S. PATENT DOCUMENTS

| | | | | |
|---|---|---|---|---|
| 4,639,604 | A * | 1/1987 | Murakami et al. | 250/548 |
| 5,610,710 | A * | 3/1997 | Canfield et al. | 356/237.6 |
| 5,889,531 | A * | 3/1999 | Koike et al. | 345/441 |
| 7,611,849 | B2 * | 11/2009 | Hansen et al. | 435/7.2 |
| 8,373,860 | B2 * | 2/2013 | Kiesel et al. | 356/417 |

(Continued)

OTHER PUBLICATIONS

Barat, D., et al., "Simultaneous high speed optical and impedance analysis of single particles with a microfluidic cytometer," Lab Chip, 12:118-126, 2012.

(Continued)

*Primary Examiner* — Isam Alsomiri
*Assistant Examiner* — Samantha K Abraham
(74) *Attorney, Agent, or Firm* — Perkins Coie LLP

(57) ABSTRACT

Techniques, devices and systems are disclosed for characterizing particles in a fluid sample by optical space-time coding. In one aspect, a microfluidic device for optical detection of particles includes a substrate, a microfluidic channel formed on the substrate and structured to carry a fluid sample containing particles, in which the microfluidic channel is structured to transmit a probe light, and a mask formed on one side of the microfluidic channel and structured to include a pattern of openings along the microfluidic channel, in which at least two of the openings have varying dimensions across the microfluidic channel, and in which the pattern of openings encodes a waveform on the probe light that transmits through the microfluidic channel to allow optical detection of a position of a particle in the microfluidic channel.

27 Claims, 20 Drawing Sheets

(56) References Cited

U.S. PATENT DOCUMENTS

| | | | |
|---|---|---|---|
| 2001/0035636 A1* | 11/2001 | Adachi | 280/735 |
| 2008/0277606 A1* | 11/2008 | Wang et al. | 250/581 |
| 2010/0297747 A1* | 11/2010 | Manalis et al. | 435/287.3 |
| 2011/0140706 A1* | 6/2011 | Groves et al. | 324/452 |
| 2013/0040837 A1* | 2/2013 | Karp et al. | 506/9 |

OTHER PUBLICATIONS

Beech, J.P., et al., "Sorting cells by size, shape and deformability," Lab Chip, 12:1048-1051, 2012.

Bhagat, A. A. S., et al., "Continuous particle separation in spiral microchannels using dean flows and differential migration," Lab Chip, 8:1906-1914, 2008.

Bhagat, A. A. S., "Inertial microfluidics for continuous particle filtration and extraction," Microfluid Nanofluid, 7:217-226, 2009.

Chen, S. C., et al., "Geometric Control of Cell Life and Death," Science, 276:1425-1428, 1997.

Cho, S.H., et al., "Human mammalian cell sorting using a highly integrated micro-fabricated fluorescence-activated cell sorter (?FACS)," Lab Chip, 10:1567-1573, 2010.

Chun, B. et al., "Inertial migration of neutrally buoyant particles in a square duct: An investigation of multiple equilibrium positions," Physics of Fluids, 18:031704, 2006.

Crawford, J., et al., "Chemotherapy-Induced Neutropenia," Cancer, 100:228-237, 2004.

Cummings, E.B., et al., "Dielectrophoresis in Microchips Containing Arrays of Insulating Posts: Theoretical and Experimental," Anal. Chem., 75:4724-4731, 2003.

Di Carlo, D., et al., "Continuous inertial focusing, ordering, and separation of particles in microchannels," PNAS, 104 (48):18892-18897, 2007.

Dochow, S., et al., "Tumour cell identification by means of Raman spectroscopy in combination with optical traps and microfluidic environments," Lab Chip, 11:1484-1490, 2011.

Downey, G.P., et al., "Retention of leukocytes in capillaries: role of cell size and deformability," Applied Physiology, 69:1767-1778, 1990.

Forbes, T.P., et al., "Microfluidic magnetophoretic separations of immunomagnetically labeled rare mammalian cells," Lab Chip, 12:1471-1479, 2012.

Godin, J., et al., "Microfluidics and photonics for Bio-System-on-a-Chip: A review of advancements in technology towards a microfluidic flow cytometry chip," J. Biophotonics, 5:355-376, 2008.

Hawkes, J. J., et al., "Continuous cell washing and mixing driven by an ultrasound standing wave within a microfluidic channel," Lab Chip, 4:446-452, 2004.

Holmes, D., et al., "Single cell impedance cytometry' for identification and counting of CD4 T-cells in human blood using impedance labels," Anal. Chem., 82:1455-1461, 2010.

Hou, H.W., et al., "Deformability based cell margination—A simple microfluidic design for malaria-infected erythrocyte separation," Lab Chip, 10:2605-2613, 2010.

Hur, S.C., et al., "Sheathless inertial cell ordering for extreme throughput flow cytometry," Lab Chip, 10:274-280, 2010.

Hur, S.C., et al., "Deformability-based cell classification and enrichment using inertial microfluidics," Lab Chip, 11: 912-92o, 2011.

Kiesel, P., et al., "Spatially modulated fluorescence emission from moving particles," Appl. Phys. Lett., 94: 041107, 2009.

Kiesel, P., et al., "Monitoring CD4 in whole blood with an optofluidic detector based on spatially modulated fluorescence emission," Cytometry A, 79:317-324, 2011.

Kilimnik, A., et al., "Inertial migration of deformable capsules in channel flow," Physics of Fluids, 23:123302, 2011.

Laxminarayan, R., et al."On the importance of incentives in hospital infection control spending," Discovery Medicine, 5(27):303-308, 2009.

Mei, Z., et al., "Applying an optical space-time coding method to enhance light scattering signals in microfluidic devices," Biomicrofluidics, 5:034116-034116-6, 2011.

Nam, J., et al., "Separation of platelets from whole blood using standing surface acoustic waves in a microchannel," Lab Chip, 11:3361-3364, 2011.

Qiao, W., et al., "Wirelessly powered microfluidic dielectrophoresis devices using printable RF circuits," Lab Chip, 11:1074-1080, 2011.

Sipsas, N.V., "Perspectives for the Management of Febrile Neutropenic Patents wth Cancer in the 21st Century," Cancer, 103:1103-1113, 2005.

Toner, M., et al., "Blood-on-a-Chip," Annu. Rev. Biomed. Eng., 7:77-103, 2000.

Watkins, N., et al., "A robust electrical microcytometer with 3-dimensional hydrofocusing," Lab Chip, 9:3177-3184, 2009.

Waugh, R.E., et al., "Chapter 32: Mechanics and deformability of hematocytes," Biomedical Engineering Fundamentals, 2nd edition, 2000.

Whitesides, G.M., "The origins and the future of microfluidics," Nature, 442:368-373, 2006.

Wu, T.F., et al., "An optical-coding method to measure particle distribution in microfluidic devices,"AIP Advances, 1:022155-022155-6, 2011.

Xuan, X., et al., "Particle focusing in microfluidic devices," Microfluid Nanofluid, 9:1-39, 2010.

Yager, P ., et al., "Microfluidic diagnostic technologies for global public health," Nature, 442:412-418, 2000.

Yun, H., et al.,"Simultaneous counting of two subsets of leukocytes using fluorescent silica nanoparticles in a sheathless microchip flow cytometer," Lab Chip, 10:3243-3254, 2010.

Zhu, J., et al., "DC dielectrophoretic focusing of particles in a serpentine microchannel," Microfluid Nanofluid, 7:751-756, 2009.

Cho, S.H., et al., "Lab-on-a-chip flow cytometer employing color-space-time coding," Appl. Phys. Lett, 97:093704-093704-3, 2010.

* cited by examiner

OPTICAL SPACE-TIME CODING TECHNIQUE IN MICROFLUIDIC DEVICES

PRIORITY CLAIM

This patent document claims the priority of U.S. provisional application No. 61/507,068 entitled "OPTICAL SPACE-TIME CODING TECHNIQUE IN MICROFLUIDIC DEVICES" filed on Jul. 12, 2011, which is incorporated by reference as part of this document.

STATEMENT REGARDING FEDERALLY SPONSORED RESEARCH OR DEVELOPMENT

This invention was made with government support under grants R21RR024453 and R43RR031424-01 awarded by the National Institutes of Health (NIH). The government has certain rights in the invention.

TECHNICAL FIELD

This patent document relates to microfluidics.

BACKGROUND

Advances in micro-electromechanical technology have enabled the fabrication of microfluidic devices integrated with various functions that can be implemented in applications related to biology and medicine. A microfluidic device is an instrument that can control the behavior of very small amounts of fluid (e.g., such as nL, pL, and fL) through channels with dimensions in relatively small dimensions, e.g., the sub-millimeter range. Microfluidic devices can be implemented to obtain a variety of analytical measurements including molecular diffusion values, chemical binding coefficients, pH values, fluid viscosity, molecular reaction kinetics, etc. Microfluidic devices can be built on microchips to detect, separate and analyze biological samples, which can also be referred to as a lab-on-a-chip. For example, a microfluidic device may use body fluids or solutions containing cells or cell parts to diagnose diseases. Inside microfluidic channels of, for example, a microfluidic flow cytometer, biological particles (e.g., including cells, beads, and macromolecules) can be interrogated according to their optical, electrical, acoustic, and magnetic responses. The positions of the samples within the microchannels can significantly affect the quality of signals, e.g., such as the value of coefficient of variation (CV).

Some techniques for positioning particles or samples inside microchannels (e.g., controlling and manipulating their positions) can be categorized into sheath and sheathless focusing approaches. Sheath focusing employs sheath fluids to narrow sample flows. Although this approach can be effective, the design can have a relatively low throughput which can become a limiting factor for certain applications. For example, for many microfluidic devices, sheath flow can confine the particles in the in-plane direction, but can require special designs and more complex processes to achieve particle confinement in the out-of-plane direction. Sheathless approaches can increase the throughput for applications that require a large volume of samples, e.g., such as milliliters of whole blood or body fluid. For example, to control particle behaviors in a sheathless design, an external force can be applied to move particles to the reestablished equilibrium positions through dielectrophoretic (DEP) effects, acoustic effects, or inertial effects induced by the balance between lifting and drag forces. For example, microfluidic devices using inertial focusing can be simple to fabricate because inertial focusing does not require additional electrodes and external signals to guide the suspended particles in the microfluidic channels.

SUMMARY

Techniques, systems, and devices are disclosed for optical detection of particles in microfluidic devices.

In one aspect of the disclosed technology, a microfluidic device for optical detection of particles includes a substrate, a microfluidic channel formed on the substrate and structured to carry a fluid sample containing particles, in which the microfluidic channel is structured to transmit a probe light, and a mask formed on one side of the microfluidic channel and structured to include a pattern of openings along the microfluidic channel, in which at least two of the openings have varying dimensions across the microfluidic channel, and in which the pattern of openings encodes a waveform on the probe light that transmits through the microfluidic channel to allow optical detection of a position of a particle in the microfluidic channel.

Implementations can optionally include one or more of the following features. The microfluidic device can further include a light source that generates the probe light through the pattern of openings to illuminate the fluid sample, in which each particle scatters the light beam to produce an optical scattering signal at each position that the particle flows along the pattern of openings of the microfluidic channel, and an optical detector arranged in a location relative to the pattern of openings to receive the optical scattering signal and produce a scattering signal waveform including signal peaks corresponding to the openings of the pattern of openings, respectively. The microfluidic device can further include a processing unit communicatively coupled to the optical detector that processes the scattering signal waveform to determine the position of the particle.

In another aspect, a method of determining a position of particle in a microfluidic channel includes transferring a fluid sample containing particles through a microfluidic channel having an pattern of apertures spatially arranged on a surface of the channel, transmitting a light beam through the pattern of apertures to illuminate the fluid sample, in which each particle scatters the light beam to produce an optical scattering signal at each position along the pattern of apertures, detecting the optical scattering signal with an optical detector configured at a scattering angle formed between the optical detector and the pattern of apertures, in which the detected optical scattering signal produces a scattering signal waveform, and processing the scattering signal waveform to determine the position of the particle in at least one dimension.

In another aspect, a microfluidic device includes a microfluidic channel structured to carry a fluid sample containing particles along a direction from an inlet region to an outlet region, the microfluidic channel including a pattern of openings spatially arranged on a surface of the channel, in which at least two openings of the pattern of openings have unequal widths along the direction, a light source that generates a light beam through the pattern of openings to illuminate the fluid sample, in which each particle scatters the light beam to produce an optical scattering signal at each position that the particle flows along the pattern of openings of the microfluidic channel, an optical detector arranged in a location relative to the pattern of openings to receive the optical scattering signal and produce a scattering signal waveform, the waveform including a signal peak corresponding to each opening of the pattern of openings, and a data processing and storage unit communicatively coupled to the optical detector, the data processing and storage unit to convert the scattering signal waveform from an analog signal format to a digital signal representation and to store the digital signal representation in a data storage.

The subject matter described in this patent document can be implemented in specific ways that provide one or more of the following features. For example, the disclosed technology includes techniques to measure the velocity and position of each particle or sample traveling through a microfluidic channel, which can produce valuable information for the design and assessment of lab-on-a-chip devices, such as flow cytometers and complete blood count devices, and point-of-care diagnostics. Particle counting and differentiation based on the disclosed optical detection techniques in microfluidic devices are cheaper, portable, and easy-to-operate, which can be used in a variety of research, clinical, environmental, and industrial applications. The disclosed technology can be used to accurately and non-invasively measure the particle distribution over the channel area under different flow conditions and particle sizes with repeatable and controllable device characteristics. The disclosed techniques can also be an advantageous in direct sequence spread spectrum technologies used in communication systems. For example, the temporarily coded signal can be easily distinguished from the noise, and the signal-to-noise ratio can be enhanced using numerous digital signal processing techniques including digital filters, matched filters, etc, enabling detection of the weak large angle scattering signals using exemplary Si PIN detector with good CV values.

DETAILED DESCRIPTION

Microfluidic technologies can be used to enable highly integrated analytical devices to perform several different functions on the same substrate, chip, or platform. For example, microfluidic-based devices can facilitate the flow of suspended particles in a microfluidic channel directed in a stream to an interrogation area where optical or electrical characterizations is performed to reveal the intrinsic properties of the sample. Such optical or electrical characterization techniques can include optical scattering, fluorescence, Raman signals, and impedance detection. For example, based on the detected signals, particle separation methods may be applied to direct the particles to the designated downstream channels. Such methods may use various mechanisms including, e.g., hydrodynamic, dielectrophoretic, optical, acoustic or magnetic mechanisms. In some implementations in which the particles include living cells, cell sorting can be used to isolate subpopulations of cells from the biological sample. For both sample analysis and sorting, detection of the intrinsic properties of each particle is an important process.

The disclosed techniques, systems, and devices can be used for optical detection of sample or particle distribution and characterization in microfluidic devices.

In one aspect, the disclosed technology includes optical coding techniques in microfluidic devices that can measure the position and velocity of particles in a microfluidic channel. For example, the disclosed technique can utilize a designed pattern of openings on the surface of the microfluidic channel as a spatial filter (or mask) to encode the scattering signal (e.g., including the forward scattering (FS) signal and/or the large-angle scattering (LAS) signal) of each individual particle. For example, the designed patterns can be deposited on the microfluidic channel area as a spatial mask to shape an illumination pattern upon the particle traveling through the detection area. The spatial mask can turn the scattering signals from traveling particles into a temporal waveform. For example, the disclosed optical coding method can be implemented to obtain the information about each particle's position and velocity and fluid dynamic properties from the waveform of the scattering signal. For example, implementation of the disclosed technology can enable means to investigate the complex relations between particle positions within microfluidic channels and flow conditions and particle sizes, as well as provide information about phenomena present within microfluidic and lab-on-a-chip devices such as inertial focusing, Dean flow, flow confinement, etc.

Figure 1A:
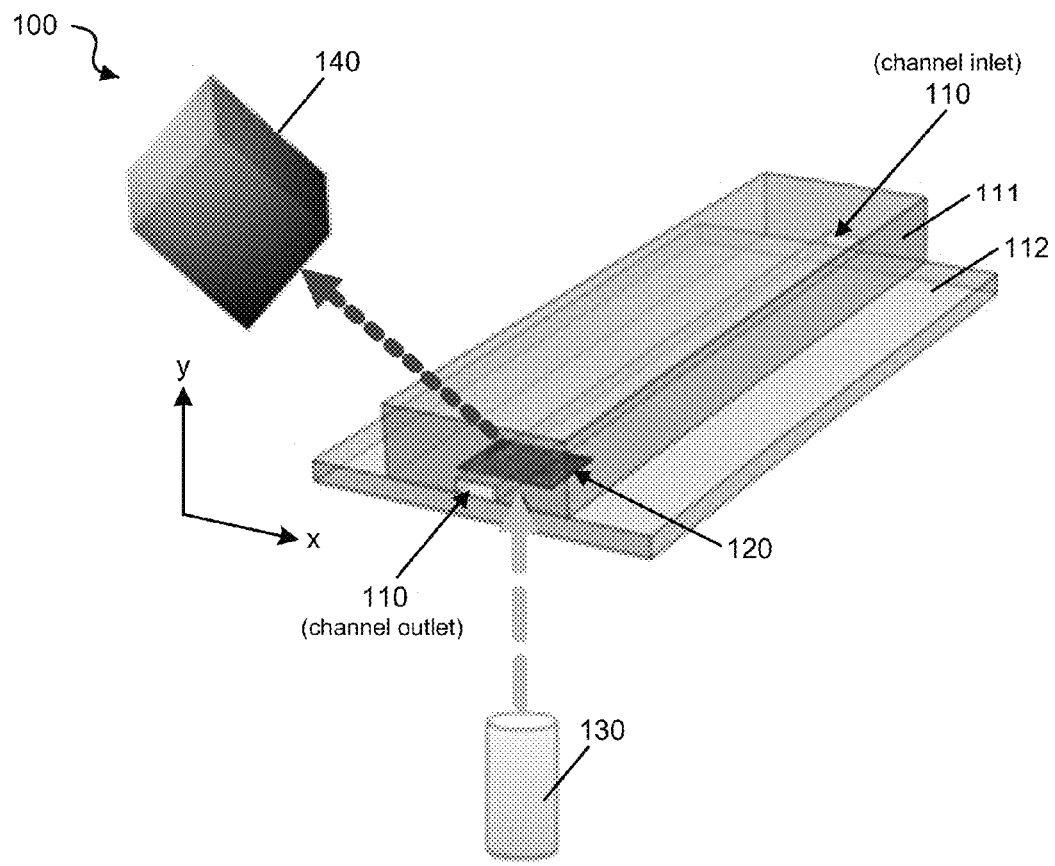
FIG. 1A shows a schematic diagram of an exemplary optical space-time coding microfluidic device of the disclosed technology.

FIG. 1A shows a schematic diagram of an exemplary optical space-time coding microfluidic device 100 of the disclosed technology. The exemplary microfluidic device 100 can be configured with at least one microfluidic channel 110 formed by a passage and structured to carry a fluid on a substrate 112. In this example, the microfluidic channel 110 may be formed in a bulk material 111 (e.g., such as polydimethylsiloxane (PDMS)) that is bonded to the substrate 112 (e.g., a glass substrate or a substrate of other material). The microfluidic device 100 includes a mask 120 located on one side of the microfluidic channel 110, in which the mask 120 includes a pattern of openings to form a particle or sample sensing area for encoding light that passes through the microfluidic channel 110 to carry space-time information. This space-time information in the light can be used to extract the location of a particle in the microfluidic channel 110 relative to the pattern of the mask 120 and to determine the speed of the particle. In the example shown, the mask 120 is located on the top surface of the microfluidic channel 110 and a probe light beam is directed to the microfluidic channel 110 from the bottom surface of the microfluidic channel 110 to interact with one or more particles in the fluid first and then enters the mask 120. Alternatively, the mask 120 may be placed on the bottom surface of the microfluidic channel 110. The output light from the mask 120 becomes spatially modulated by the pattern of openings in the mask 120 to indicate the position of a particular particle with respect to the mask 120. The duration of time at a particular opening for the particle is used to determine the speed of the particle based on a dimension of the opening.

The microfluidic device 100 includes a light source 130 that generates the probe beam that is filtered through the pattern of openings of the mask 120. For example, the light source 130 can include a laser source such as a semiconductor laser diode, e.g., a semiconductor laser diode, or a Hg-arc lamp, among other light sources. The probe beam may be in various wavelengths and power levels, e.g., 20 mW in power and at 650 nm in wavelength. The filtered light can be received by a photodetector 140 (e.g., silicon (Si) PIN photodiode) located on the opposite end of the microfluidic device 100 from the light source 130. For example, the photodetector 140 can include a PIN silicon photoreceiver to collect 5~10 degree forward scattering signals. In some examples, additional optics can be used between the light source (e.g., laser) and the detector to enhance the detection of scattering signals. In other examples, such as of a robust and low maintenance system, no optics may be used between the light source (e.g., laser) and the detector other than orienting the detector ~7 degrees from the exemplary laser beam for forward scattering detection. The output signal of the photodetector 140 can be directed to a processing system that can include an A/D circuit with an amplifier. The processing system processes the space-time information on the filtered light to extract the position and velocity information of a particle.

Particles can be deployed in the microfluidic device 100 to flow through the microfluidic channel 110. For example, to obtain a desired flow speed, a fluid pump can be incorporated and the sample loading and flow rate can be set internally, e.g., requiring no attention from users. Forward scattering signals can be produced by the particles scattering the filtered light passing through the mask 120 that exhibit distinct waveforms in time domain. The waveforms can be detected by the photodetector 140 that interfaces with the processing system that can determine the positions and velocities of these particles in the microfluidic channel.

In one example, the microfluidic channel 110 can be configured to be 5 cm long in the longitudinal direction (z) of the channel between an inlet and an outlet at the end of the channel. The exemplary channel can be configured to have a rectangular cross section with a width of 100 μm along the transverse direction (x) of the channel and a height of 45 μm along the y direction. In this example shown in FIG. 1A, the exemplary channel width is defined along the x-axis and the exemplary channel height is defined along y-axis. For example, the mask 120 can be placed at 4.5 cm from the inlet of the microfluidic channel 110.

The pattern of openings in the mask 120 can be designed to have predefined geometry and dimension along the longitudinal direction (z) and transverse direction (x) of the microfluidic channel 110 to enable determination of the location of a particle within the pattern. Each opening can have a varying opening dimension at different positions across the channel, e.g., along the transverse or lateral direction of the channel (x direction). The variation of the opening dimension of each opening at different positions across the channel in the x direction is a monotonic function of the x position so that a unique opening dimension value (e.g., an opening width W1, W2, W3 or W4) is given for a unique x position in the channel. Under this design, a measurement of the opening width along the channel allows determination of the x position of a particle. Also, at a given x position in the channel, the opening dimensions along the longitudinal direction (z direction) of the channel of two adjacent openings are different. Such features of the openings provide spatial information encoding on light passing through the channel to determine the location of a particle within the mask.

Figure 1B:
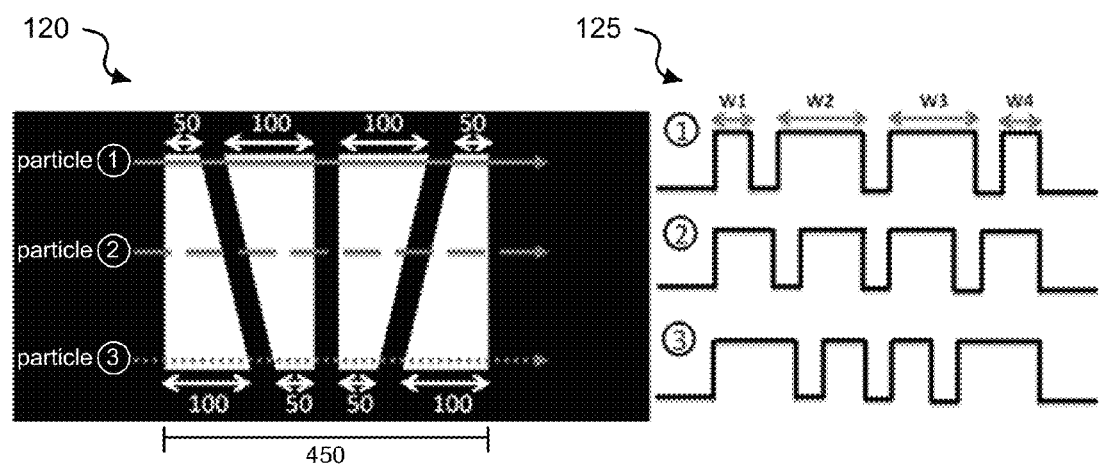
FIG. 1B shows a diagram of an exemplary spatial pattern for optical coding.

FIG. 1B shows a diagram of an exemplary spatial pattern of the mask 120 for optical coding in the exemplary microfluidic device 100. For example, the pattern of openings of the mask 120 can include a pattern of four trapezoidal slits, e.g., in which each exemplary trapezoidal slit includes base lengths of 100 μm and 50 μm along the z direction arranged in an alternating pattern with a separation of 50 μm along the z direction, with a total pattern length of 450 μm. The trapezoidal shape of each slit produces a varying length of each slit with respect to the transverse direction x to enable determination of the x position of a particle. An exemplary forward scattering signal of each particle passing through the exemplary spatial pattern of the mask 120 exhibits a specific waveform according to the lateral position (transverse position) through which the particle travels, as illustrated by the waveform plot 125 for three exemplary waveforms of three particles traveling at three different lateral (transverse) positions along the x direction in the channel 110. For example, three representative forward-scattering signals are shown in the plot 125 corresponding to three exemplary particles traveling through different lateral positions of the microfluidic channel 110. The exemplary detected intensity-modulated FS signal (e.g., modulated by the exemplary trapezoidal slits of the mask 120) displays four peaks, e.g., W1, W2, W3, and W4, corresponding to the four sequential trapezoidal slits. The width of each peak in the signal can be used to acquire the position of particles along the x-direction. The particle speed or velocity can be further determined from such a detected waveform.

In addition to determination of a particle position in the transverse or lateral direction x of the channel 110, the disclosed technology can also provide a method to obtain the particle position along channel depth or height along the y-axis based on the particle velocity traveling along the z direction. For example, knowing the position in the x-axis and the velocity along the z direction, the cell position in the y-axis can be obtained using the property of laminar flow that gives rise to a parabolic velocity profile. In microchannels, a laminar flow is formed due to the low Reynold number (Re), as expressed in $Re=\rho U_f D_h/\mu$, where $\rho$ represents the fluid density, $U_f$ represents the average velocity of flow, $D_h$ represents the hydraulic diameter of microchannels, and $\mu$ represents the fluid viscosity. As a result, at a given particle position along the width (x-direction) of the channel, the velocity profile along the out-of-plane (y-axis) direction obeys, to a good approximation, the parabolic characteristics:

$$\upsilon(x,y)=\upsilon_{Max}(x)[1-(y/h)^2] \quad (1)$$

where $\upsilon$ is the velocity at a specific position (x, y), $\upsilon_{Max}$ is the velocity at position x and the middle of the channel (e.g., at y=0), and h is the half-depth of the channel (e.g., 22.5 μm in the exemplary implementations described herein). Therefore, $\upsilon_{Max}$ can be obtained at each position x from an exemplary fluid dynamic simulation, and the position y of the particle can be obtained from its velocity using Eq. (1). This described relation provides an accurate approximation when W/h>>1, and the relation between cell speed and cell position is highly reproducible due to the nature of laminar flow in a microfluidic channel.

The mask 120 is designed to include two or more openings with varying lengths along the z direction so that a particle at different lateral or transverse position in the channel would have different waveforms as shown in FIG. 1B. For example, in FIG. 1B, the ratio between the width of the first peak (W1) and the second peak (W2) can yield information about the particle's position in the x-axis. In this example, the first two openings on the left of the mask 120 would be sufficient. In this specific example, the pattern of the mask 120 further includes two more trapezoidal slits on the right side of the mask 120 to provide spatial redundancy. In this example, the two more trapezoidal slits on the right side of the mask 120 are identically shaped with the first two slits and are symmetrically arranged along the channel (z direction). The ratio of W4 and W3 can also be used to independently determine x and y position of a particle and the particle velocity. The redundancy introduced in this example can be used to reduce noise and improve measurement accuracy, as well as distinguish one type of particle from another. The velocity of the particle can be acquired by dividing the total pattern length (e.g., 450 μm) by the duration of signal. For example, by knowing the position in the x-axis and the velocity of the particle, the particle's position in the y-axis can be obtained using the property of laminar flow.

In one example of the microfluidic device for optical detection of particles, the exemplary microfluidic device can include a substrate, a microfluidic channel formed on the substrate and structured to carry a fluid sample containing particles, in which the microfluidic channel is structured to transmit a probe light, and a mask formed on one side of the microfluidic channel and structured to include a pattern of openings along the microfluidic channel, in which at least two of the openings have varying dimensions across the microfluidic channel, and in which the pattern of openings encodes a waveform on the probe light that transmits through the microfluidic channel to allow optical detection of a position of a particle in the microfluidic channel. Also, for example, the exemplary microfluidic device can further include a light source that generates the probe light through the pattern of openings to illuminate the fluid sample, in which each particle scatters the light beam to produce an optical scattering signal at each position that the particle flows along the pattern of openings of the microfluidic channel, and an optical detector arranged in a location relative to the pattern of openings to receive the optical scattering signal and produce a scattering signal waveform including signal peaks corresponding to the openings of the pattern of openings, respectively. The microfluidic device can further include a processing unit communicatively coupled to the optical detector that processes the scattering signal waveform to determine the position of the particle.

The disclosed technology includes signal processing algorithms and techniques for cell classification and counting. For example, the exemplary signal processing techniques can be implemented to remove noise and baseline drift of forward scattering signals, manage coincident events (e.g., when more than one particle or cell travels through the detection area simultaneously), obtain forward scattering intensity, cell velocity, and cell position (x-, y- and z-positions) from the raw signals, and create automatic gating for cell count and classification.

For example, an exemplary signal processing technique can include signal filtering of the received scattering signals, e.g., including first implementing a high pass filter and then a low pass filter on the received scattering signals to remove noise and baseline drift. The exemplary signal processing techniques can detect the rising and falling edges of each received signal peak that reaches a threshold value. For example, in the case of the sample including living cells, a single cell event should produce four rising and falling edges passing through the exemplary detection area 120 of the microfluidic channel 110 (e.g., as shown in FIGS. 1A and 1B). If either the number or the parity is inconsistent, the event can be attributed as a coincident event where more than one cell passed the detection area. Such coincident events can be tracked in the processing unit and discerned in the final determination of the cell count. For example, in 5 μL of RBC lysed whole blood that is diluted to 1 mL buffer, X neutrophils, Y lymphocytes, and Z coincident events can be counted. By eliminating the chance of triple-incident events due to their low probability, then the real number of neutrophils ($X_N$) and lymphocytes ($Y_L$) can be obtained by solving the following equations (2) and (3).

$$X_N = X + \frac{2X_N X_N + X_N Y_L}{(X_N X_N + X_N Y_L + Y_L Y_L)} Z \quad (2)$$

$$Y_L = Y + \frac{2Y_L Y_L + X_N Y_L}{(X_N X_N + X_N Y_L + Y_L Y_L)} Z \quad (3)$$

The exemplary microfluidic device 100 may produce more coincident events due to lack of sheath flow confinement, which can be processed by the exemplary techniques to detect and register the coincident events and obtain the absolute cell count using the above relations. The exemplary signal processing and data analysis algorithms will be implemented in Matlab, or in other programs implemented in the processing unit. In some examples, the exemplary signal processing and data analysis algorithms can be downloaded by general users and implemented on an independent and/or external processing system, such as a user's personal computer, a portable computing device such as a tablet or smartphone, or other computing device. In such examples, raw data received by the photodetector can be offloaded to the independent and/or external processing system. In some exemplary implementations, the disclosed optical space-time microfluidic technology can include a graphic user interface (GUI) to allow skilled users to choose gating parameters of the cell distributions. In other exemplary implementations, all gating parameters can be defined automatically without user inputs (e.g., which can be useful in home point-of-care devices and systems designed for use by patients directly or other unskilled users).

Exemplary fabrication processes and implementations were performed to demonstrate the functionalities and capabilities of the disclosed technology. For example, a microfluidic device with a straight channel was fabricated in polydimethylsiloxane (e.g., using Sylgard 184, Dow Corning) bonded to a glass substrate. The microfluidic channel was 5 cm long and included a cross-section of 100 μm×45 μm (width× height). The exemplary sensing area where the forward scattering signal was detected included a mask having pattern openings of four transparent trapezoidal slits. The exemplary spatial mask was formed by patterning a thin Ti/Au metal film on the glass substrate. Each trapezoidal slit included base lengths of 100 μm and 50 μm. The exemplary four slits were separated by 50 μm between each other and located 4.5 cm from the inlet. A 488 nm wavelength diode laser (e.g., 40 mW, Spectra-physics) was used as the optical source for the forward scattering measurement. The beam spot of the laser included a Gaussian intensity profile across the whole sensing area of 450 μm. A silicon photodetector (e.g., PDA36A, Thorlabs) was placed over the microfluidic device to collect 5~10 degree forward scattering signals from exemplary particles deployed through the microfluidic channel over sensing area. For example, a mixture of polystyrene beads with diameters of 5, 10 and 15 μm (e.g., PPS-6K, Sphero) was injected into the microchannel with the flow rate controlled by a syringe pump (NE-1000, New Era Pump Systems). For example, because of the unequal width for each slit, the deployed particles within the exemplary microfluidic channel produce forward scattering signals with four peaks of different widths in the time domain. The optical-coded forward scattering signals were processed using a processing script (e.g., using MATLAB) with standard filtering techniques; and the results determined the particle position along the direction of channel width, e.g., defined as the x-axis, and velocity for each particle. The exemplary processing script was also implemented to identify the types of particles by the intensity of forward scattering signals.

The disclosed optical-coding technique can be employed to obtain particle distributions in a microfluidic channel under different flow conditions. After processing the forward scattering signals encoded by a specially designed spatial mask, the position and velocity of each particle in a sample can be obtained, which can provide information about the behaviors of different particles in microfluidic channels. Exemplary implementations using various types of particles (e.g., polystyrene beads and living cells) were performed to demonstrate the disclosed technology ability to produce the spatial distribution of particles within the microfluidic channel. The disclosed technology can be implemented in stand-alone devices or integrated into microfluidic lab-on-a-chip devices and systems such as cell sorters and flow cytometers in a wide variety of applications, e.g., including microfluidic biomedical devices.

Figure 2:
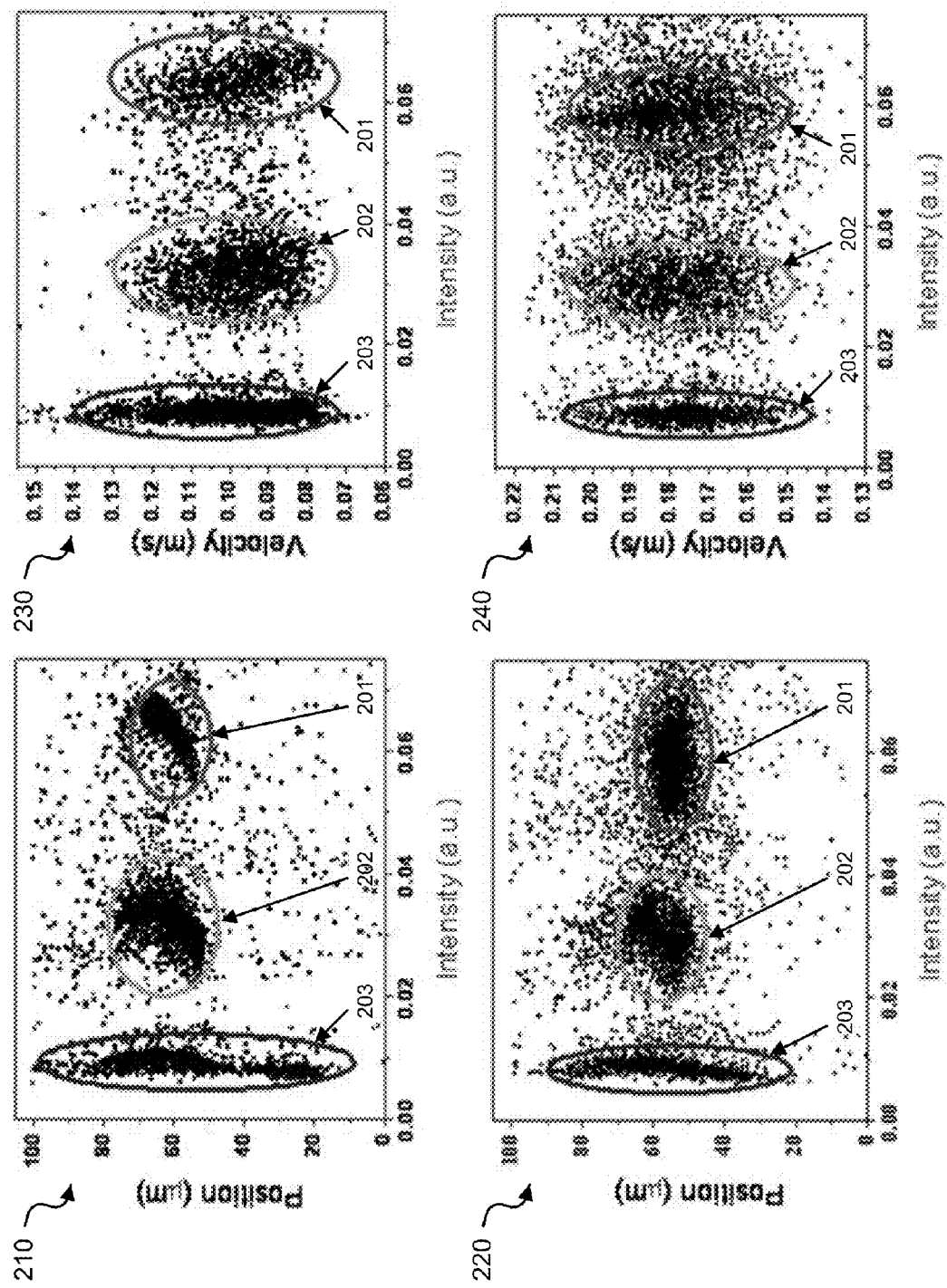
FIG. 2 shows scatter plots of particle position versus forward scattering (FS) intensity and particle velocity versus intensity using an exemplary optical coding microfluidic device.

Exemplary implementations were performed that included deploying a mixture of various polystyrene beads with 5, 10 and 15 μm sized diameters into an exemplary microchannel at controlled flow rates. FIG. 2 shows exemplary scatter plots 210 and 220 of particle position along the x-axis versus forward scattering intensity at flow rates of 25 μL/min and 50 μL/min respectively, and exemplary scatter plots 230 and 240 of particle velocity versus FS intensity at the flow rates of 25 μL/min and 50 μL/min, respectively. For example, approximately 5000 events were processed and exhibited three distinct populations shown in each data plot of FIG. 2, e.g., 15 μm sized beads (circle 201), 10 μm sized beads (circle 202), and 5 μm sized beads (circle 203). For example, the position of each particle along the x-axis was determined by the width ratio of the first peak (W1) to the second peak (W2) as well as the width ratio of the fourth peak (W4) to the third peak (W3). The velocity of each particle was obtained by dividing the pattern length, 450 μm, with the overall duration of the signal. The resultant data of the exemplary implementations demonstrated that the particles with different sizes can be discriminated using the disclosed optical coding microfluidic technology by their forward scattering intensity.

Figure 3A:
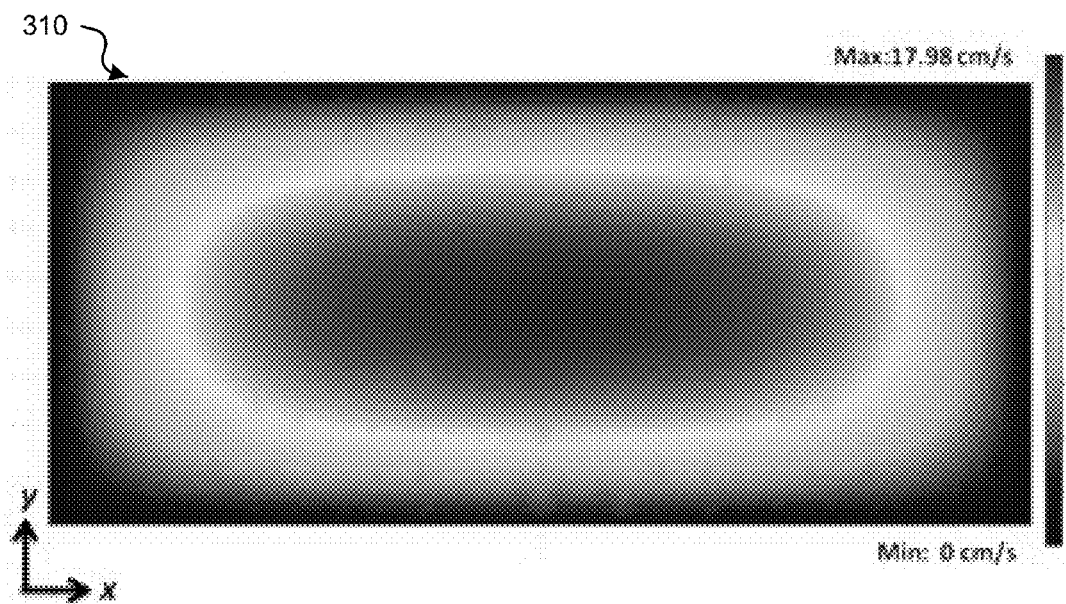
FIGS. 3A and 3B show data plots of simulated flow velocity profiles on the x-y plane.
Figure 3B:
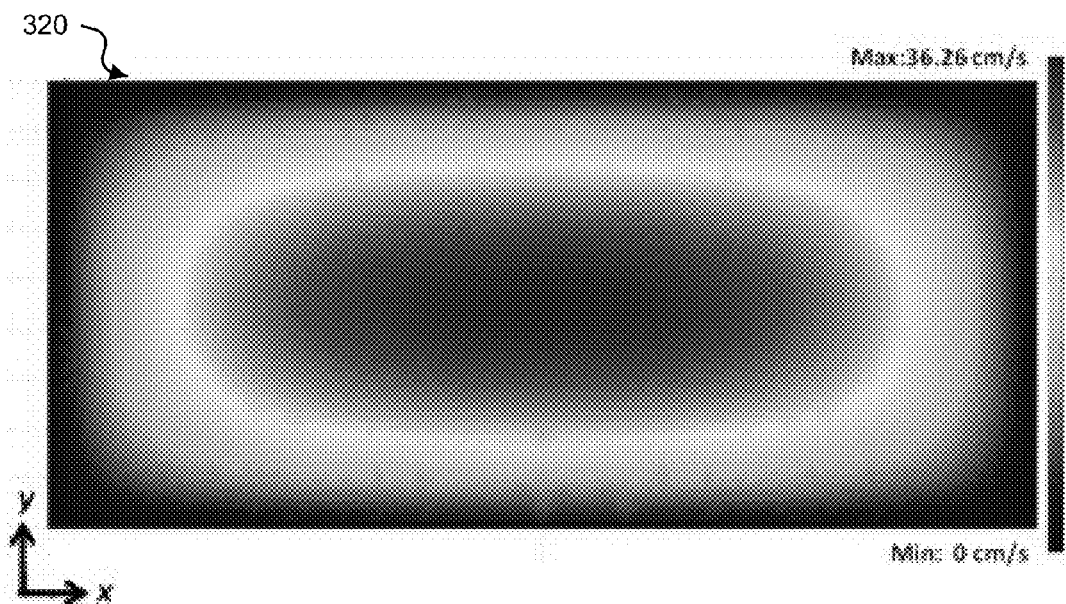

FIG. 3A shows a data plot 310 of exemplary simulated flow velocity profile on the x-y plane at a flow rate of 25 μL/min. FIG. 3B shows a data plot 320 of exemplary simulated flow velocity profile on the x-y plane at a flow rate of 50 μL/min. For example, an exemplary microfluidic device was used in exemplary implementations that included a rectangular microchannel cross-section with a $D_h$ (hydraulic diameter of the microchannels) of 62.1 μm. The measured average velocity using the 25 μL/min flow rate was determined to be 0.09 m/s, e.g., resulting in Re (Reynold number) of 5.59. The measured average velocity using the 50 μL/min flow rate was determined to be 0.18 m/s f, e.g., resulting in Re (Reynold number) of 11.18. These exemplary measured average velocities were shown to agree with the values calculated from exemplary COMSOL simulations (e.g., shown in data plots 310 and 320), e.g., which demonstrated the effective use of the simulated $\upsilon_{Max}(\chi)$ to determine the out-of-plane position of the particle, y, from Eq. (1).

Figure 4A:
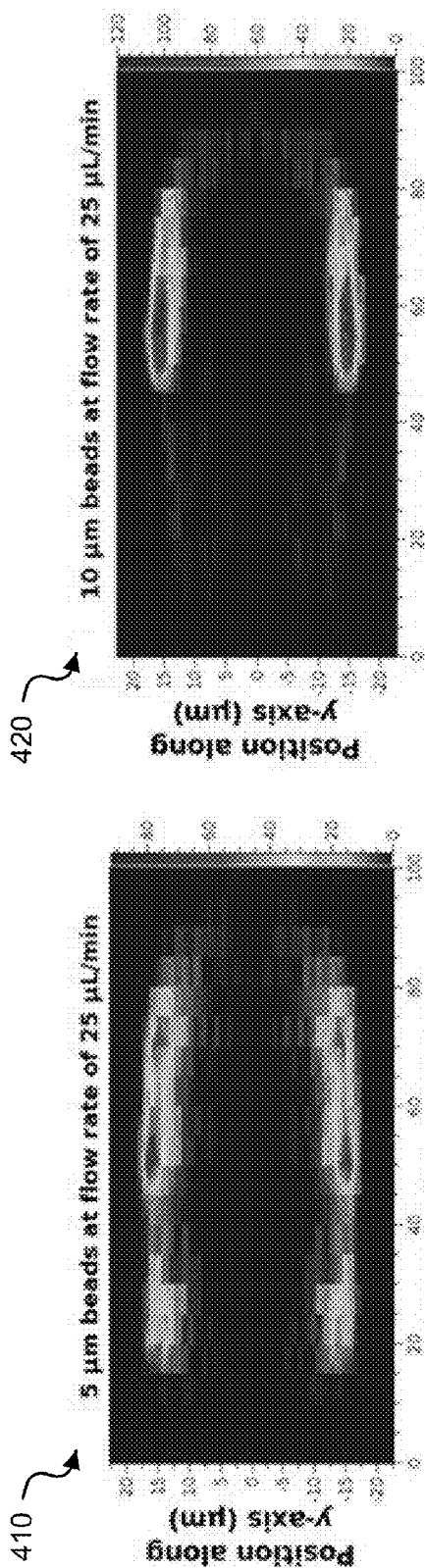
FIGS. 4A-4D show spatial distribution plots of particles within exemplary microfluidic channels.
Figure 4B:
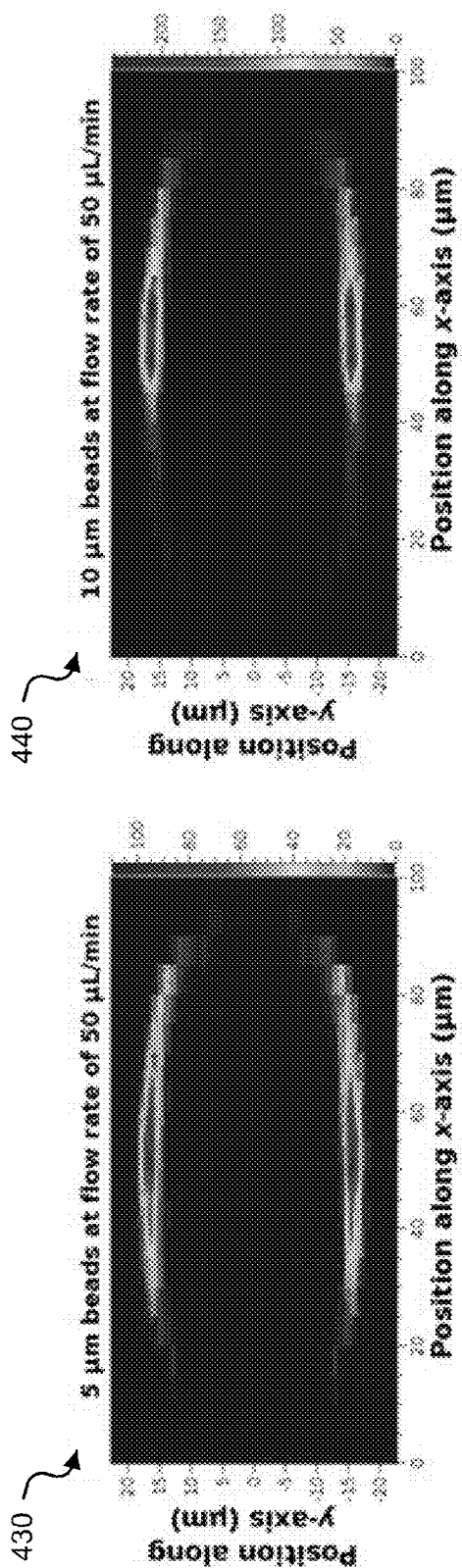
Figure 4C:
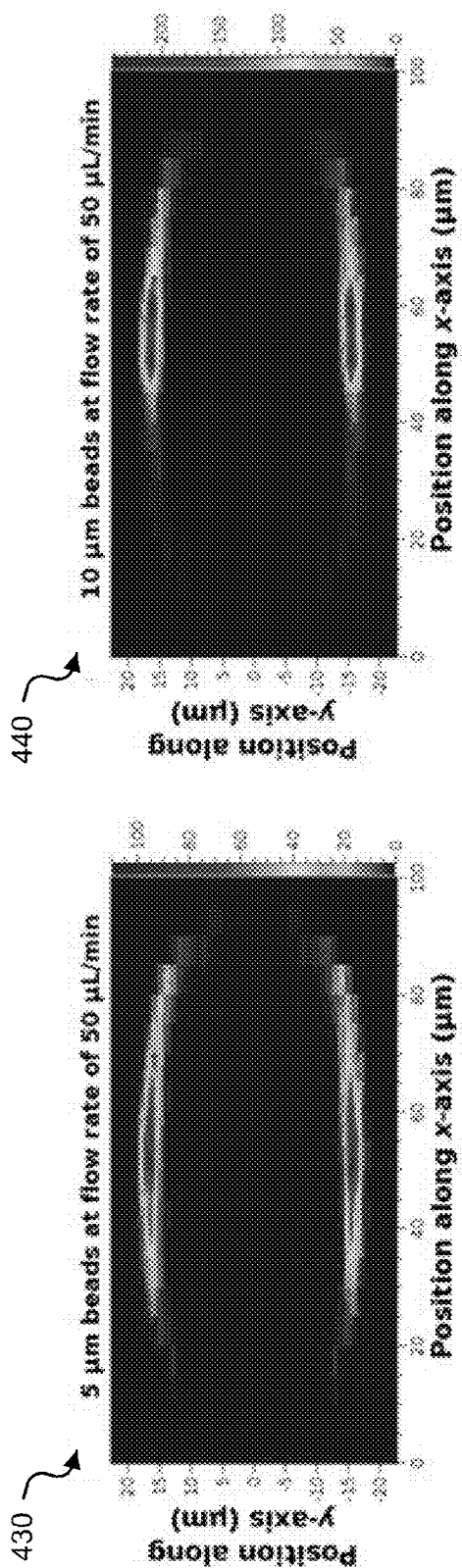
Figure 4D:
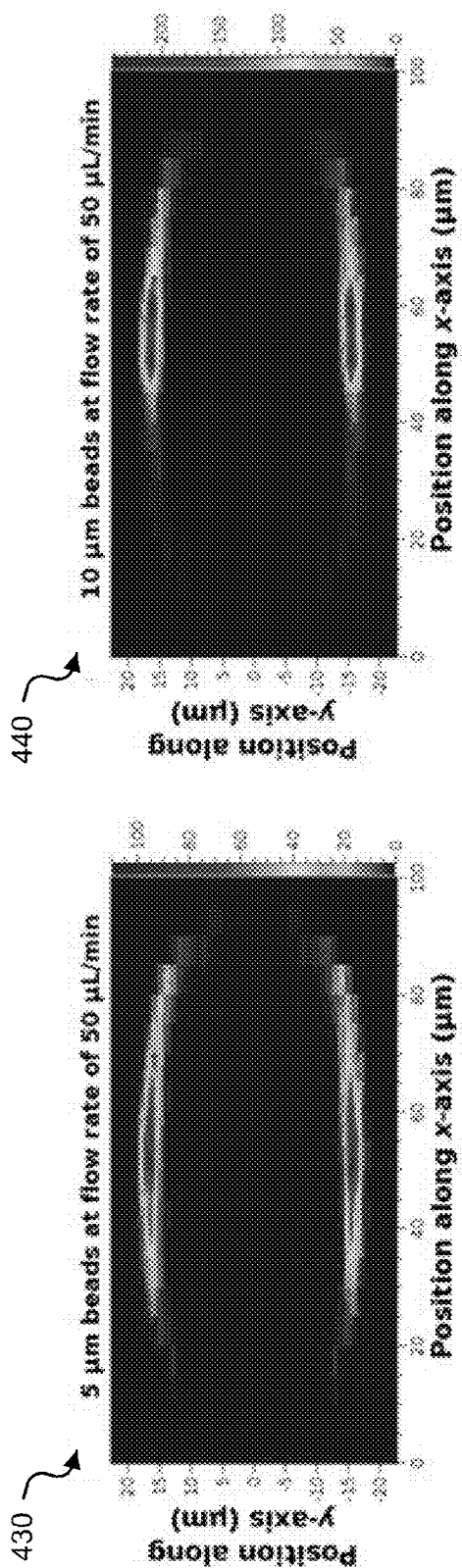

FIGS. 4A-4D show exemplary spatial distribution plots of particles within microfluidic channels. FIG. 4A shows a data plot 410 for 5 μm beads at a flow rate of 25 μL/min. FIG. 4B shows a data plot 420 for 10 μm beads at a flow rate of 25 μL/min. FIG. 4C shows a data plot 430 for 5 μm beads at a flow rate of 50 μL/min. FIG. 4D shows a data plot 440 for 10 μm beads at a flow rate of 50 μL/min. The color bar in the data plots shows the frequency of microbeads population. These exemplary results show that the stable positions for both 5 μm and 10 μm beads were 8.3 μm away from the channel wall (e.g., ±14 μm from center) under a flow rate of 25 μL/min and ~6.8 μm away from the channel wall (e.g., ~±16 μm from center) under a flow rate of 50 μL/min. For example, the exemplary results indicate that particles migrate closer to the wall as Re increases; and under these exemplary parameters, the lift force drives particles to positions that are ~0.2 H away from the walls, where H represents the characteristic dimension (e.g., height of the microchannel for the exemplary device geometry). In addition, for example, along the x-axis, larger particles were more concentrated toward the center of the channel. Such distinct phenomena in the particle distributions along the x-(width) and y-(height) axes were consistent with the results predicted by the fluidic dynamic theory for inertial focusing. For example, the lift force can be represented as $F_L = \rho G^2 C_L d^4$, where G is the fluid shear rate (G=2 $U_f/H$), $C_L$ is the lift coefficient (which for microchannels remains constant), and d is the particle diameter. In the exemplary device geometry (e.g., as shown in FIG. 1B), the width to height ratio is larger than 2, which resulted in a lift force in the y-direction four times greater than the force in the x-direction due to different shear rates. This effect causes particles to migrate toward the longer channel walls to find the equilibrium positions. Concerning the lift force in the x-direction, its magnitude can depend on the size of particles to the $4^{th}$ power so the lift force of 10 μm beads is 16 times of the lift force of 5 μm beads. For example, the greater lift force can lead larger beads to be farther away from the walls of shorter dimension and show a narrower distribution than the smaller beads, e.g., which is consistent with the results in FIGS. 4A-4D.

Figure 5A:
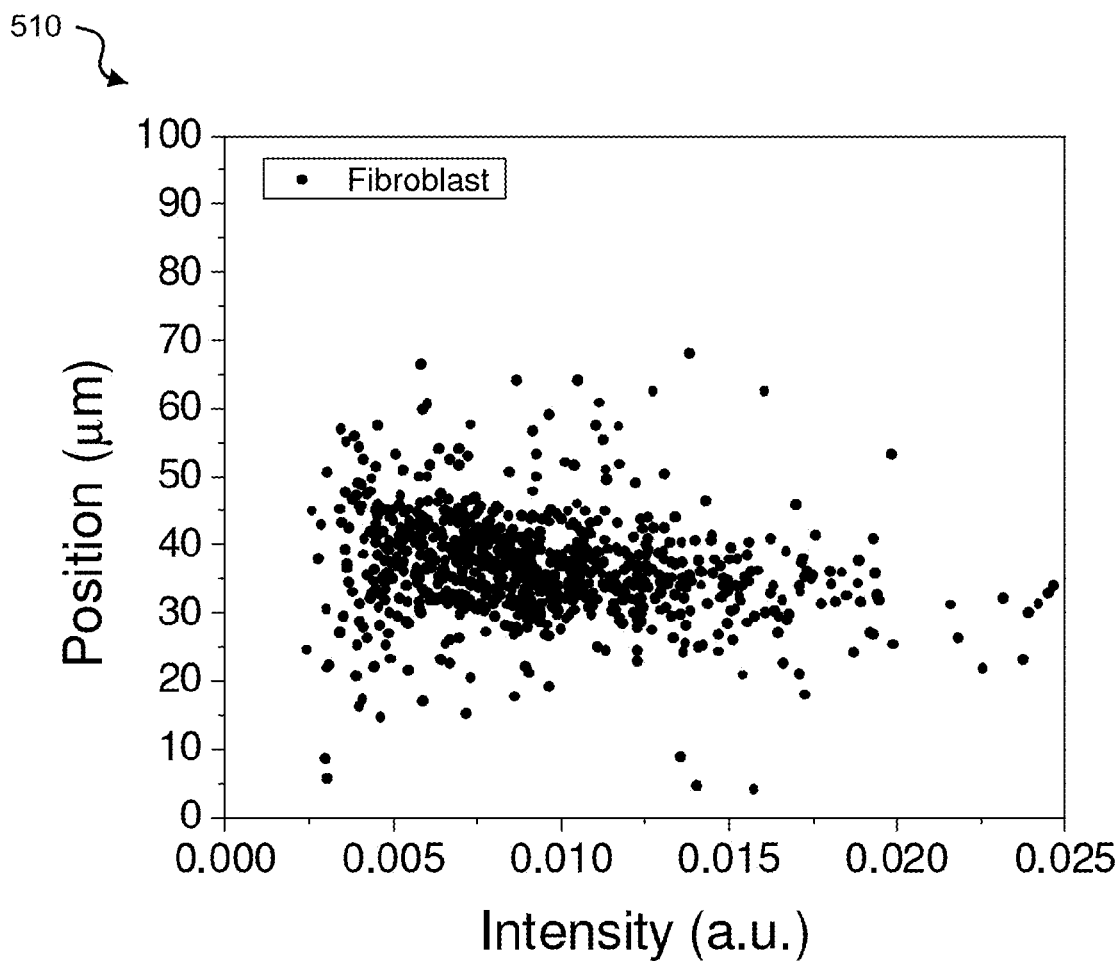
FIG. 5A shows a scatter plot of fibroblast position versus FS intensity using an exemplary optical coding microfluidic device.
Figure 5B:
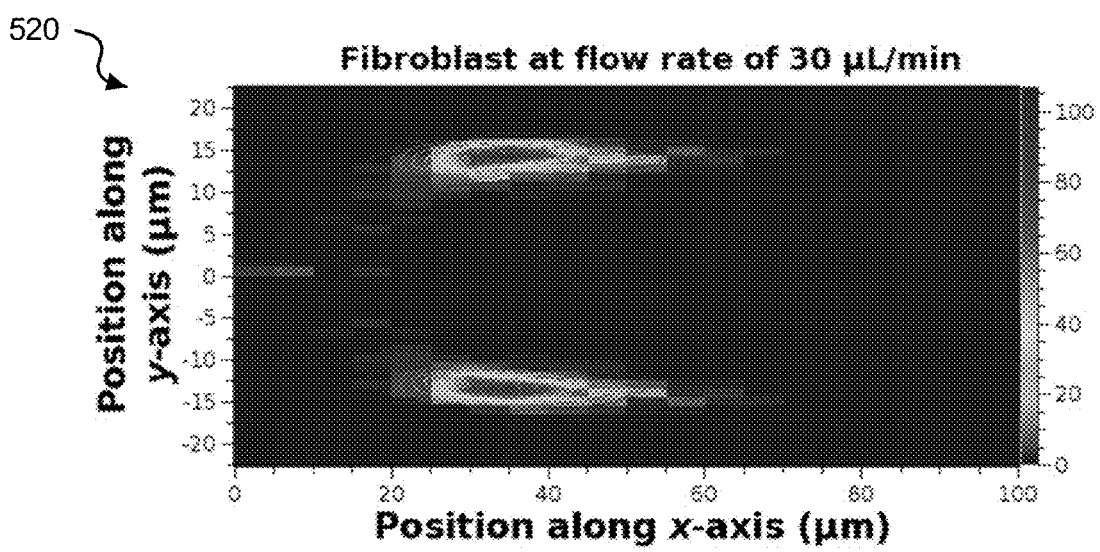
FIG. 5B shows a spatial distribution plot of fibroblasts within the exemplary microfluidic channel.

Exemplary implementations of the disclosed technology for cell detection were performed, e.g., using fibroblast cells at a flow rate of 30 μL/min. FIG. 5A shows a scatter plot 510 of fibroblast position along x-axis versus forward scattering intensity using an exemplary microfluidic device of the disclosed technology. FIG. 5B shows a data plot 520 of spatial distribution of fibroblasts within the microfluidic channel at the flow rate of 30 μL/min. For example, approximately 1000 events were detected and processed, with the results shown in the exemplary scatter plot 510. For example, fibroblasts have a typical size of around 15 μm, and the cell focusing effect was demonstrated in the exemplary spatial distribution plot 520. For example, due to the depth and angle of tube insertion to the microfluidic devices, the particle distribution along the x-direction may show bias from the center of the channel; and the disclosed method can faithfully reveal such effects of interfacing the macro- and micro-fluidic environments. The exemplary implementations were performed at sample speeds between 5 cm/s and 20 cm/s, e.g., which can be typical values for many applications using flow cytometers, cell counters, complete blood counts, etc.). The disclosed optical coding method can be applied to higher sample speeds for high throughput applications, e.g., as the exemplary Si photoreceiver can include a large gain-bandwidth product (e.g., >10 MHz).

In another implementation, the disclosed technology includes optical coding techniques using forward scattering (FS) signals (e.g., 5-10 degrees) and large angle scattering (LAS) (e.g., 45-60 degrees) or side-scattering (SS) signals, or a combination thereof, in microfluidic devices for particle analysis. The exemplary microfluidic devices and techniques can reveal the size, shape, and granularity of each individual particle without the need for labeling. Exemplary implementations were performed using the disclosed optical space-time coding method applied to microfluidic devices to detect the FS and LAS signals for unlabelled bead and cell detection.

Figure 6A:
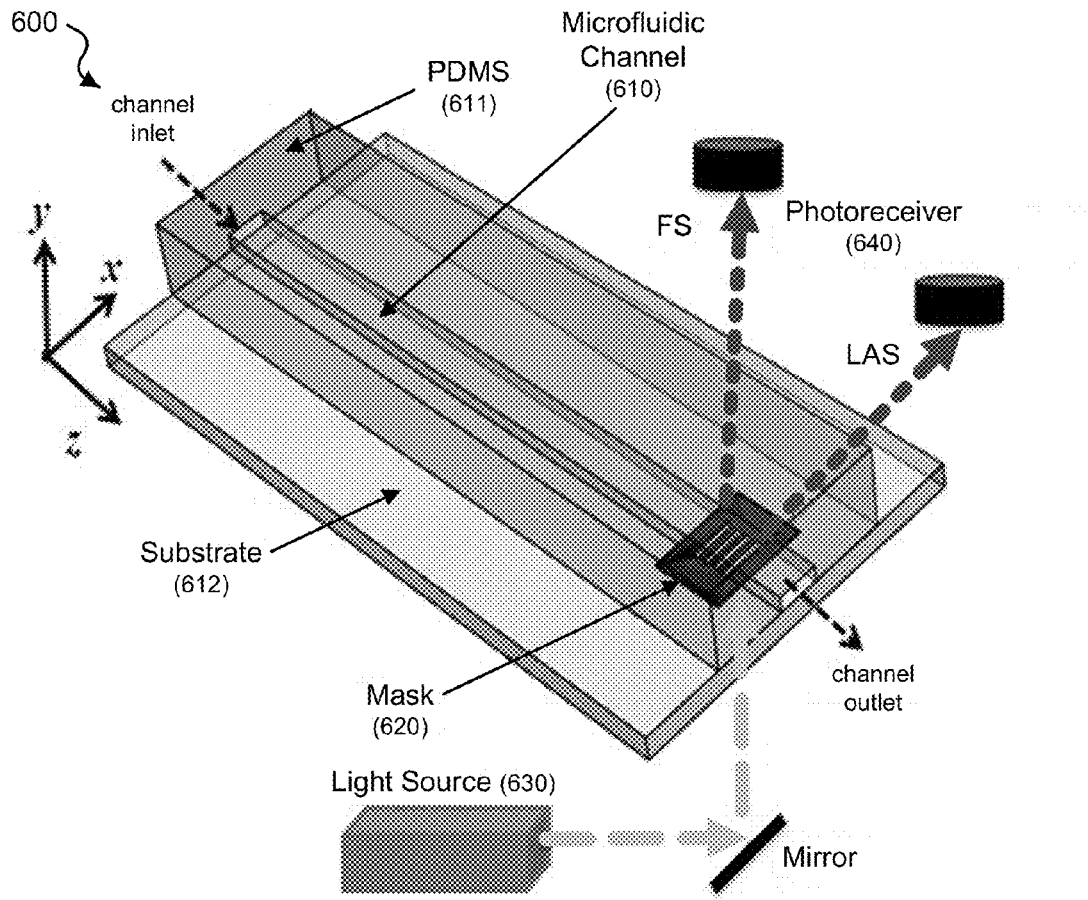
FIG. 6A shows a schematic diagram of an exemplary optical space-time coding microfluidic device of the disclosed technology.

FIG. 6A shows a schematic diagram of an exemplary optical space-time coding microfluidic device 600. The exemplary microfluidic device 600 can be configured with at least one microfluidic channel 610 formed by a passage along a surface of a bulk material 611 (e.g., PDMS) that is bonded to a substrate 612 (e.g., such as a glass substrate). In this example, the microfluidic channel 610 of the microfluidic device 600 is a straight channel that includes a spatial mask 620 having a pattern of openings to form a sample sensing area. The microfluidic device 600 includes a light source 630 that can generate and transmit a beam of light that is filtered through the pattern of openings of the spatial mask 620 as it enters the microfluidic channel 610. For example, the light source 630 can include a laser source such as a semiconductor laser diode (e.g., 40 mW 488 nm wavelength diode laser), or a mercury arc lamp, among other light sources. The exemplary microfluidic device 600 can include one or more minors to direct the beam of light to the spatial mask 620 of the microfluidic channel 610. The filtered light can form a Gaussian intensity profile across the sensing area and be received by one or more photoreceivers 640 (e.g., silicon (Si) PIN photodiode) located on the opposite end of the microfluidic device 600 from the light source 630. For example, the two exemplary silicon photoreceivers 640 can be placed over the microfluidic device 600 to detect FS and LAS synchronously from particles passing the sensing area. For example, the two exemplary silicon photoreceivers 640 can include Si PIN photoreceivers with a 3×3 $mm^2$ photosensitive area. Samples containing particles can be deployed in the microfluidic device 600 to flow through the microfluidic channel 610. Samples can enter the microfluidic channel 610 from the inlet by a syringe pump. For example, FS and/or LAS signals can be produced by the particles scattering the filtered light passing through the mask 620 that exhibit distinct waveforms in time domain. The waveforms can be detected by the photoreceivers 640 that interfaces with a processing system that can determine the positions and velocities of these particles in the microfluidic channel. For example, the scattering signals can be collected by signal detection software (e.g., Signal Express, National Instrument) and processed with digital signal processing software (e.g., Matlab, MathWorks) installed on a standard desktop computer. In some examples, the processing system of the exemplary microfluidic device 600 can include signal processing such as a high pass digital filter (e.g., cutoff frequency of 250 Hz) to remove low frequency noise and any base line drift from the detected scattering signals (e.g., FS and LAS). For example, the gain of the signal amplifier can be configured to 50 dB for LAS detection and 30 dB for FS detection, e.g., since the LAS signals are much weaker than FS signals. The processing system of the exemplary microfluidic device 600 can include standard peak-finding algorithm(s) based on predefined threshold(s) (e.g., employed in Matlab) to register all detectable events.

For example, the exemplary microfluidic device 600 with the spatial mask 620 can be fabricated in PDMS using standard soft lithography techniques. The straight microfluidic channel 610 can be configured with a 5 cm in length with a cross-section of 100 μm×45 μm (width (along the x-axis)× height (along the y-axis)). The interrogation area of the spatial mask 620 where the scattering signal is detected can be configured in a pattern like that shown in FIG. 6B. For example, four transparent trapezoidal slits can be formed as a spatial mask by patterning a thin Ti/Au metal film on the glass substrate. Each trapezoidal slit can include base lengths of 100 μm and 50 μm. The four exemplary slits can be separated by 50 μm spacing between each other, located 4.5 cm from the inlet.

Figure 6B:
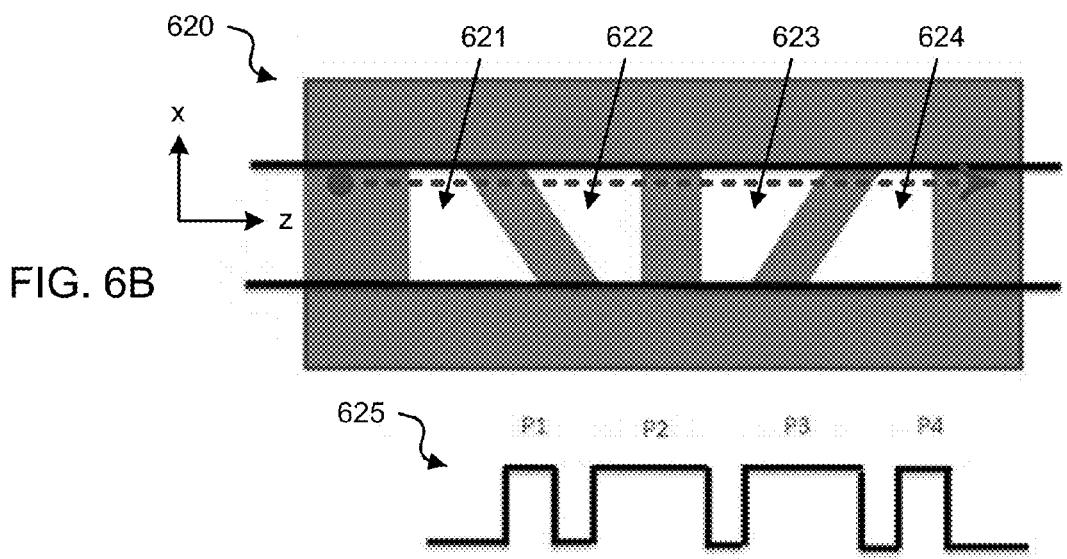
FIG. 6B shows a diagram of an exemplary spatial pattern for optical coding.

As shown in FIG. 6B, a scatting signal of a specific waveform 625 is generated by the four transparent slits 621, 622, 623, and 624 corresponding to the position of a particle 629 that passes through the spatial mask 620 along either of the mask edges. For example, because of the exemplary trapezoid slit pattern design, the ratio of pulse widths P2 to P1 of the waveform 625 is between 2 and 0.5. In this exemplary spatial mask design, ratio values 2 and 0.5 correspond to two opposite ends of the mask or the edges of the microfluidic channel. A P2/P1 ratio value of 1 corresponds to the center of the channel along the channel width. The velocity of each particle can also be obtained by dividing the pattern width (e.g., 450 µm) by the duration of the waveform.

The exemplary microfluidic device 600 can be configured without the use of flow confinement or sheath flow mechanisms, e.g., which can reduce the complexity of device fabrication and operation without affecting the functionality of the optical space-time coding features. As a result, for example, coincident events (e.g., two or more particles simultaneously passing the interrogation area) may occur more frequently than microfluidic devices with sheath flow. Coincident events can be detected by the exemplary microfluidic device 600 since such coincident events lack the four distinctive peaks which are characteristics of signals from single events. Signals produced by coincident events (e.g., more than one particle passing the detection regime) can be identified by the exemplary microfluidic device 600 based on the redundancy of pattern openings in the spatial mask 620. For example, the exemplary transparent slits 621 and 622 are repeated in a mirrored configuration by the exemplary transparent slits 623 and 624. Thus, for example, two or more particles passing through the interrogation area of the spatial mask 620 would produce a non-mirrored waveform indicative of the coincident event detected by the photoreceivers 640 that interfaces with the processing system. The processing system can isolate coincident events from the non-coincident events and perform parallel processing to decipher the number of particles and their intrinsic properties from the captured waveform.

Figure 7A:
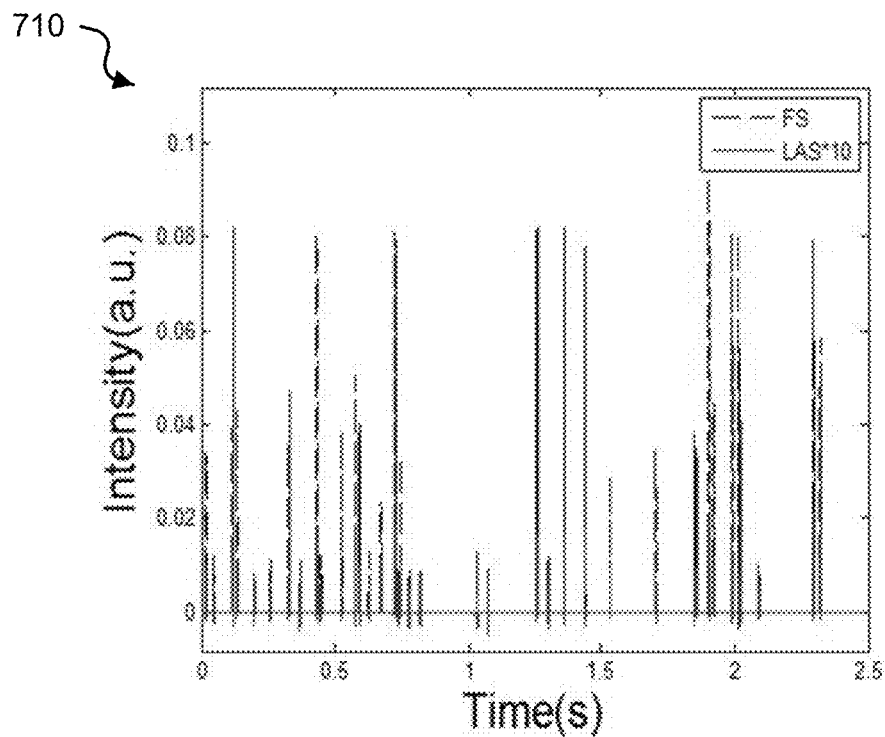
FIGS. 7A and 7B show data plots of exemplary space-time coded FS and large angle scattering (LAS) signals produced by polystyrene bead samples.
Figure 7B:
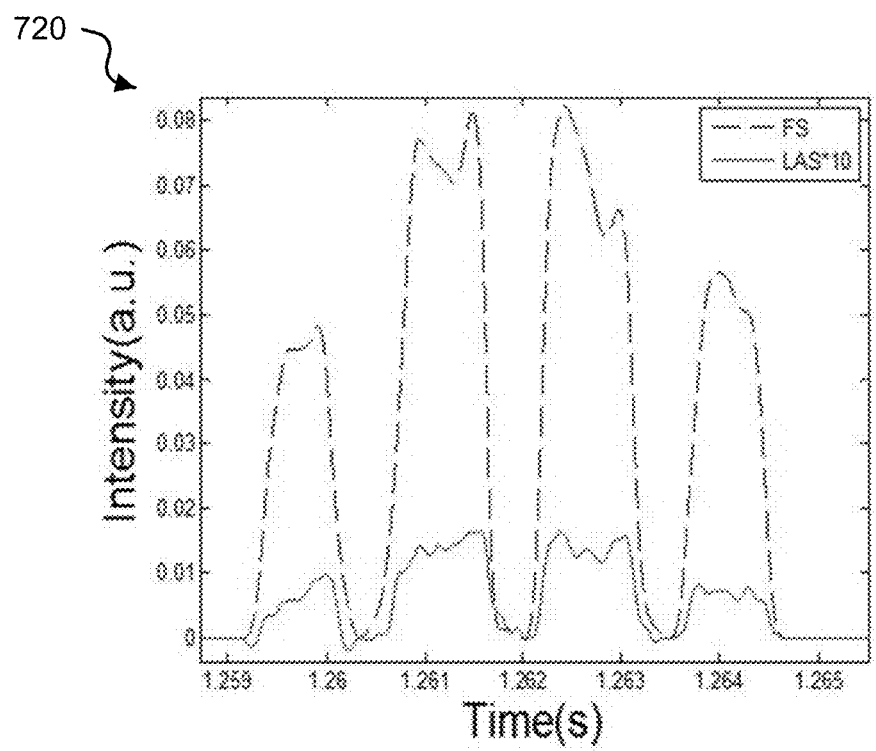

Exemplary implementations were performed that included deploying a mixture of various polystyrene beads with 5, 10 and 15 µm sized diameters into the exemplary microfluidic device 600. FIGS. 7A and 7B show data plots of exemplary space-time coded FS and LAS signals produced by the polystyrene bead samples. FIG. 7A shows a data plot 710 of forward scattering signal intensity (FS, blue-dashed line) and large angle scattering intensity (LAS×10, red-solid lines) versus time for a mixture of 5, 10 and 15 µm beads. To show both signals on the same chart, the LAS signals were also plotted at 10× of the measured amplitudes. FIG. 7B shows a data plot 720 featuring a close-up view of one event. All signals plotted in the data plots 710 and 720 are signals after pre-processing by a low pass filter with a cutoff frequency of 2500 Hz. For example, due to the Gaussian intensity profile of the laser beam, the two central peaks of the space-time coded signals have higher magnitudes than the two side peaks. The quality of the signals, particularly the more noisy LAS signals, can be enhanced using several digital signal processing algorithms enabled by their special waveforms. Such algorithms include matched filter, cross correlation between the stronger FS signal and the weaker LAS signal, etc. For example, in the exemplary implementations described, the processing algorithms included just the average of the magnitudes of the four distinct peaks in the waveform. The exemplary data in FIGS. 7A and 7B showed that this exemplary processing algorithm significantly improved the CV values of both FS and LAS signals, while also requiring a minimum amount of computation power, e.g., which can favor real-time processing required in cell sorting applications.

Figure 8:
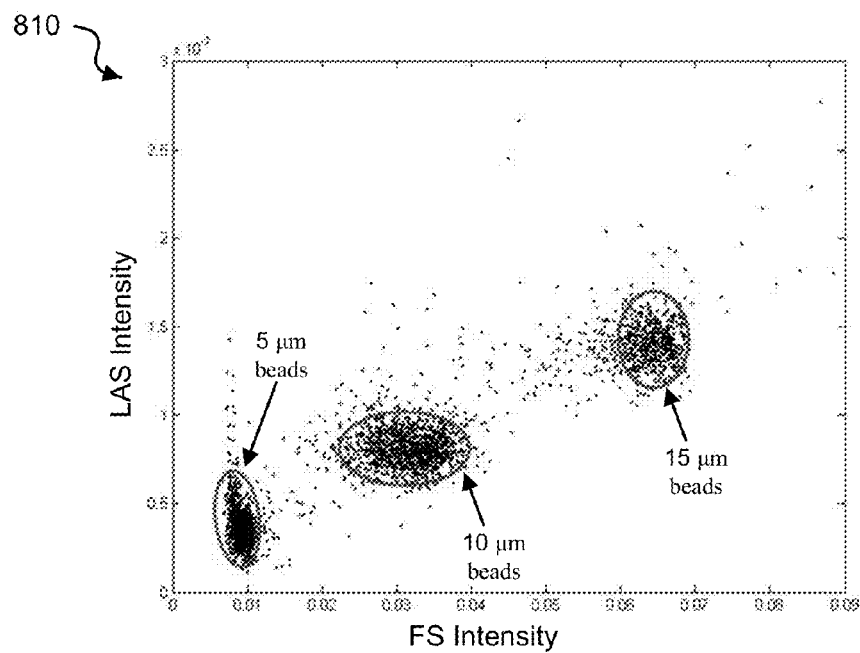
FIG. 8 shows a scatter plot of the distribution of LAS intensity versus FS intensity from a sample of polystyrene beads using an exemplary optical coding microfluidic device.

FIG. 8 shows a scatter plot 810 of the distribution of LAS intensity versus FS intensity from a sample including a mixture of 5 µm, 10 µm and 15 µm polystyrene beads using an exemplary optical coding microfluidic device of the disclosed technology at a flow rate of 25 µL/min. As shown in the scatter plot 810, the larger beads produce higher FS and LAS intensities and three types of beads form three separate clusters that are easy to distinguish. It is noted, for example, that some data points exist in ambiguous regions between the clusters, e.g., perhaps due to intrinsic bead size variation or damaged beads. By employing the quadrant gate, the scatter intensity CVs of each bead population are summarized in Table 1.

TABLE 1

| Scatter Intensity CVs | | |
| --- | --- | --- |
| | FS CV | LAS CV |
| 5 µm | 10.05% | 26.12% |
| 10 µm | 9.53% | 11.5% |
| 15 µm | 3.95% | 7.97% |

The disclosed optical space-time coding technology can offer capabilities to measure the position and velocity of each particle in the microfluidic channel. For example, the velocity information can be obtained from the spacing between the pattern openings of the spatial mask and the time difference between the peaks in the waveform. For example, based on the special design of the spatial mask (e.g., as shown in FIG. 6B), there exists a relation between the ratio of the pulse width of each peak and the position of the particle, as previously described.

Figures 9A, 9B:
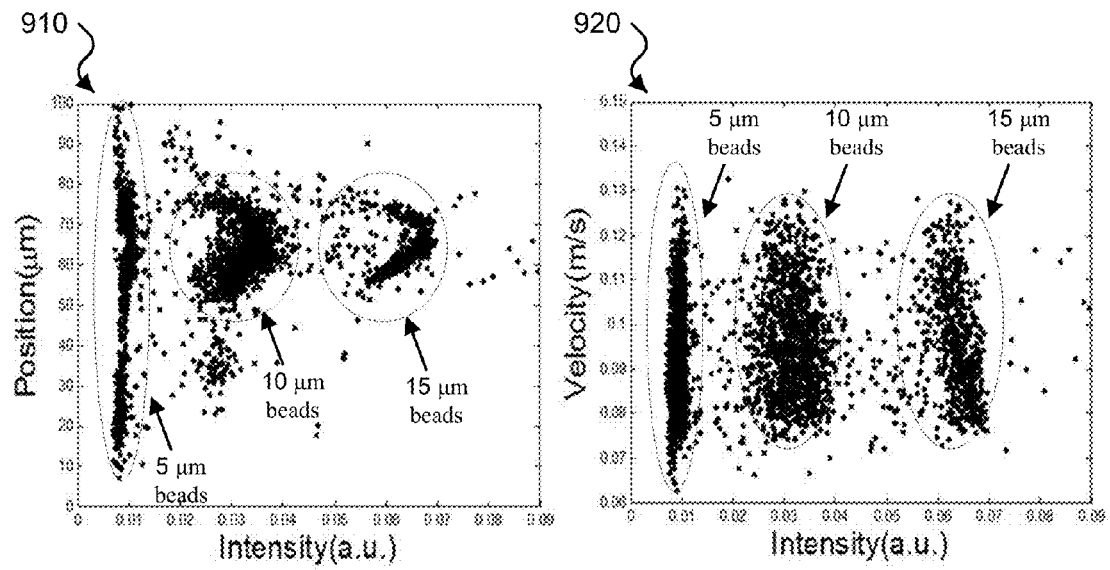
FIGS. 9A and 9B show data plots of the distribution of bead position and velocity versus FS intensity.

FIGS. 9A and 9B show data plots of the distribution of bead position versus FS intensity (data plot 910 of FIG. 9A) and velocity versus FS intensity (data plot 920 of FIG. 9B) for the mixture of 5 µm, 10 µm, and 15 µm beads at a flow rate of 25 µL/min. For example, the exemplary implementation included approximately 3000 events that were processed. The exemplary data in the data plot 910 suggest that, without flow focusing or sheath flow, 5 µm beads spread widely over the entire 100 µm width of the microfluidic channel whereas 10 µm and 15 µm beads were more concentrated to a narrow range of the channel. This exemplary result demonstrates the effect of inertial focusing governed by the particle Reynolds number. The results also shed light on the feasibility and effectiveness of using fluid dynamics properties to separate particles. On the other hand, for example, data in FIG. 9B show that beads of all three sizes had similar velocity distributions, except, for example, a lower number of 10 µm and 15 µm beads had lower speed because they were further away from the channel edge.

Figure 10A:
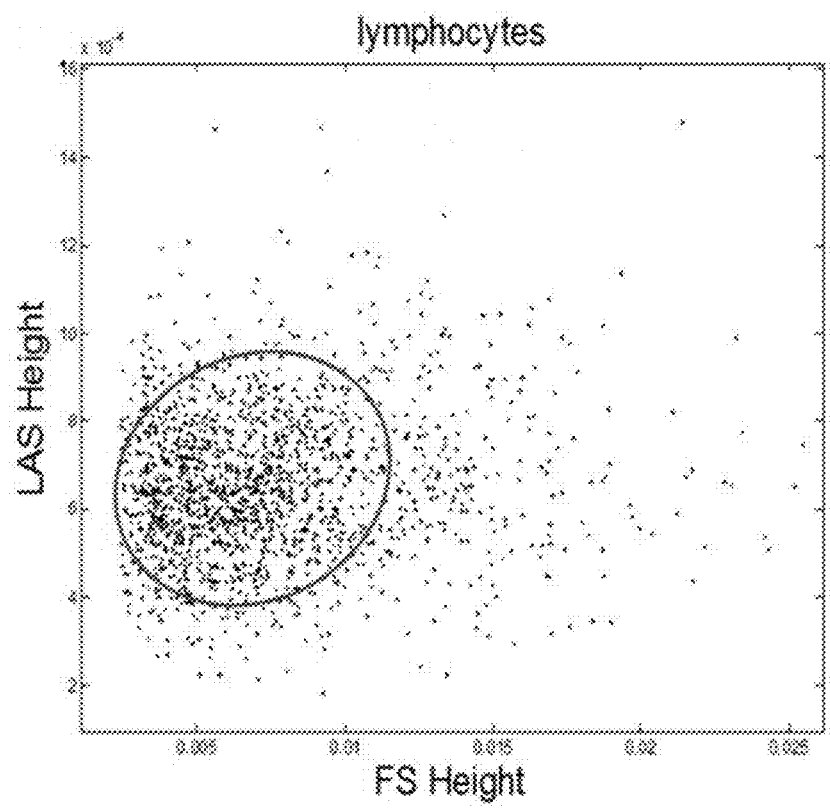
FIGS. 10A-10B show a scatter plot of the distribution of FS versus LAS intensity from a sample of lymphocyte cells using an exemplary optical coding microfluidic device.
Figure 10B:
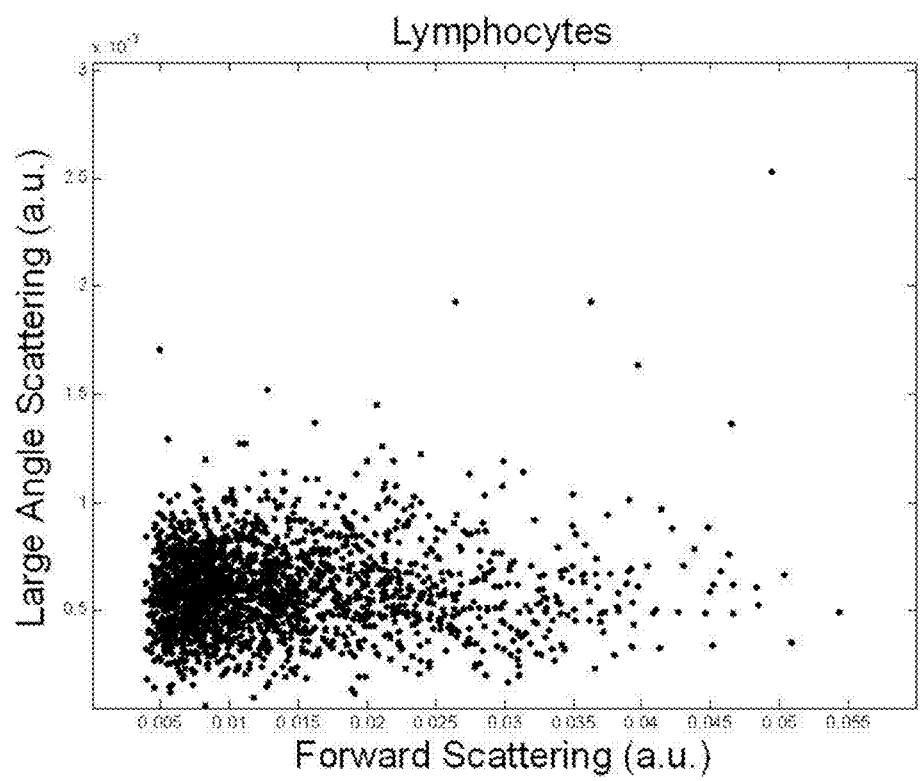

FIG. 10A shows a scatter plot 1000 of the distribution of LAS intensity versus FS intensity from a sample of lymphocyte cells using an exemplary optical coding microfluidic device of the disclosed technology at a flow rate of 25 µL/min. The plot 1000 shows a wide distribution in the intensity of FS and LAS signals, e.g., which can be attributed to the intrinsic characteristics of lymphocyte. It is noted that, for example, no system noise near the origin of the plot was present in the exemplary device, e.g., as exemplary signal processing algorithms can be implemented to remove the background noise. FIG. 10B shows another scatter plot 1050 of the distribution of LAS intensity versus FS intensity from a sample of lymphocyte cells using the exemplary optical coding microfluidic device.

Figure 11:
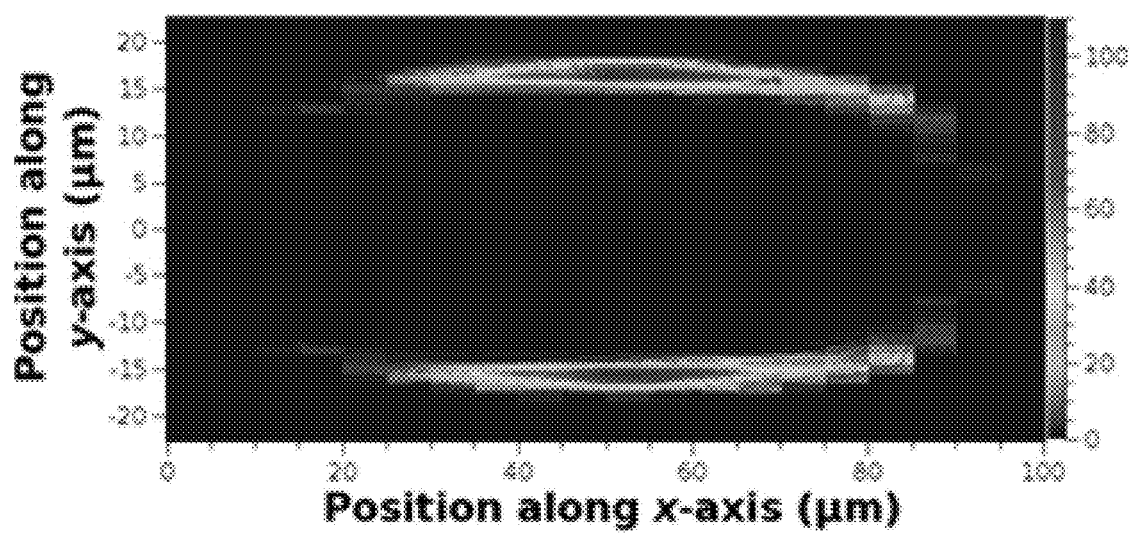
FIG. 11 shows an illustration of spatial pattern for optical coding.

FIG. 11 shows a contour plot 1100 of the spatial distribution of 5 µm beads over the cross-section of the exemplary microfluidic channel, e.g., based on particle-by-particle measurements without averaging. The color bar in the plot 1100 shows the frequency of beads.

In another aspect, the disclosed technology includes optical coding microfluidic (optofluidic) lab-on-a-chip device that can measure optically encoded scattering signals (e.g., including FS, LAS, and SS). The disclosed optofluidic device includes a sensing area within a microfluidic channel designed with spatially coded patterns that modulate the excitation light intensity experienced by the particle passing the patterns to measure the position and velocity of each particle (e.g., such as living cells) in a sample flow and a processing unit that generates particle characterization and distribution data (e.g., including 2-D cell distribution plots over the cross section of the channel). The disclosed optofluidic technology can be implemented on a lab-on-a-chip microfluidic platform that uses the described space-time coding method to measure the position of each cell traveling in the microfluidic channel and uses the fluidic dynamic properties influenced by cell deformability and cell volume to differentiate cell types, e.g., neutrophils from other blood cells such as lymphocytes. For example, the disclosed optofluidic device can effectively convert a spatial pattern (code) into an optical intensity-modulated time-domain signal that can be readily processed by digital signal processing (DSP) algorithms. For example, the disclosed optofluidic device can characterize living cells and determine their distribution within a sample based on their size and stiffness. For example, cell stiffness is a biomarker that can be used for cell classification, and the disclosed technology can be used to classify cells by their stiffness.

Currently, most sophisticated equipment for cell-based assays is located in major medical centers. For example, the high cost for equipment acquisition, maintenance, and medical personnel, as well as the support of the massive outfit and infrastructure contributes to the high and rising health care cost in most developed countries, particularly the United States. Additionally, the lack of such sophisticated medical equipment in resource limited countries and territories, on the other hand, presents major challenges in delivering quality health care services to populations living in these areas. For example, detection and classification of cells using sophisticated tools such as flow cytometers and fluorescence-activated-cell-sorters (FACS) can be clinically utilized for disease diagnosis and prognosis. However, performing such tests in point-of-care clinics or patient's residence can reduce cost, time from test to outcome, as well as chances for hospital infection. To do such, lab-on-a-chip and point-of-care devices should be able to generate reliable results, easy to operate, compact and affordable.

The optofluidic methods, devices and systems of the disclosed technology can be used in a variety of specific biomedical applications that target specific biomarkers without labeling or sample preparation. For example, the present optofluidic technology can use cell stiffness as the biomarker for cellular characterization and determination of various conditions and certain diseases, e.g., as stiffness of cells is cell-type specific and also provides information about the health and life cycle of cells. The present method of optical space-time coding enables unambiguously measurement of the position of each cell traveling in the microfluidic channel of an exemplary optofluidic device. Using the principle that the stable positions of cells in a microfluidic channel depend upon cell size and stiffness, cells are classified by their stiffness in the flow channel at very high throughput. The optofluidic detection method requires no sheath flow for flow confinement. The disclosed optofluidic technology is compact, inexpensive, and simple to fabricate and operate. For example, exemplary optofluidic devices can be implemented in a variety of point-of-care and home-care applications, e.g., such as important clinical applications that measure the immune functions of patients such as cancer patients undergoing chemotherapy.

In some examples, since the space-time coded signal is carried in both forward and side scattering signals, the disclosed technology can be configured to only detect the forward scattering signal, from which all additional information (position and velocity) can be obtained. This can make the system simple, robust, compact and inexpensive, since the forward scattering signal is orders of magnitude stronger than side scattering signal and thus requires no sophisticated optics or photomultiplier tubes (PMTs) to perform the measurements.

Blood and other bodily fluids such as urine are samples that are easy to acquire with minimal invasiveness, and such samples, particularly blood, contain rich health and disease information. The disclosed technology can be implemented to characterize and classify cells within the blood without performing blood preparation processes, such as steps including anticoagulation, centrifuge, anti-body labeling or staining, filtering, etc. Exemplary implementations were performed to characterize and distinguish living cells within whole blood using an exemplary optofluidic device of the disclosed technology. For example, the exemplary optofluidic device was used to detect neutrophil cells from other blood cells in a whole blood sample based on cell stiffness properties.

For example, neutrophils are an important indicator for the functions of the immune system. Neutrophil cells are the most abundant white blood cell, taking between 53-62% of the total white blood cell population. Neutrophils are granulocytes named by the shape of its nucleus and are softer than monocytes and lymphocytes, a property that facilitates its migration to the sites of infection from blood vessels. Clinically, a patient is considered to be in mild neutropenia if the neutrophil count in the blood is between 1000 and 1500/μL, in moderate neutropenia when the neutrophil density drops to 500-10004/μL, and in severe neutropenia when the density falls below 500/μL. Severe neutropenia leads to very high risk of infection, which could be life threatening particularly for cancer patients undergoing chemotherapy. Each year over 90,000 patient deaths result from hospital infection in the United States. Cancer patients undergoing chemotherapy typically make 12 to 24 hospital visits, often times only for neutrophil counts.

Table 2 includes properties of blood cells. In Table 2, the numbers in the cell diameter column in italic inside ( )* represent dimensions for cells on glass slides, and the numbers outside ( )* represent dimensions when cells are suspended in the fluid.

TABLE 2

| | Occurrence (% of WBCs) | Cell volume (μm³) | Cell diameter (μm) | Nucleus (% Cell volume) | Cortical tension (mN/m) |
|---|---|---|---|---|---|
| Granulocytes | | | | | |
| Neutrophils | 50-70 | 300-310 | 8.2-8.4 (10-14)* | 21 | 0.024-0.035 |
| Basophils | 0-1 | | (8-14)* | | |
| Eosinophils | 1-3 | | (10-14)* | 18 | |
| Monocytes | 1-5 | 400 | 9.1 (12-18)* | 26 | 0.06 |
| Lymphocytes | 20-40 | 220 | 7.5 (8-12)* | 44 | 0.035 |
| Red blood cells | | 96 | (7.5-8)* | 0 | 0.5 0.006 (bending) |

Figure 12A:
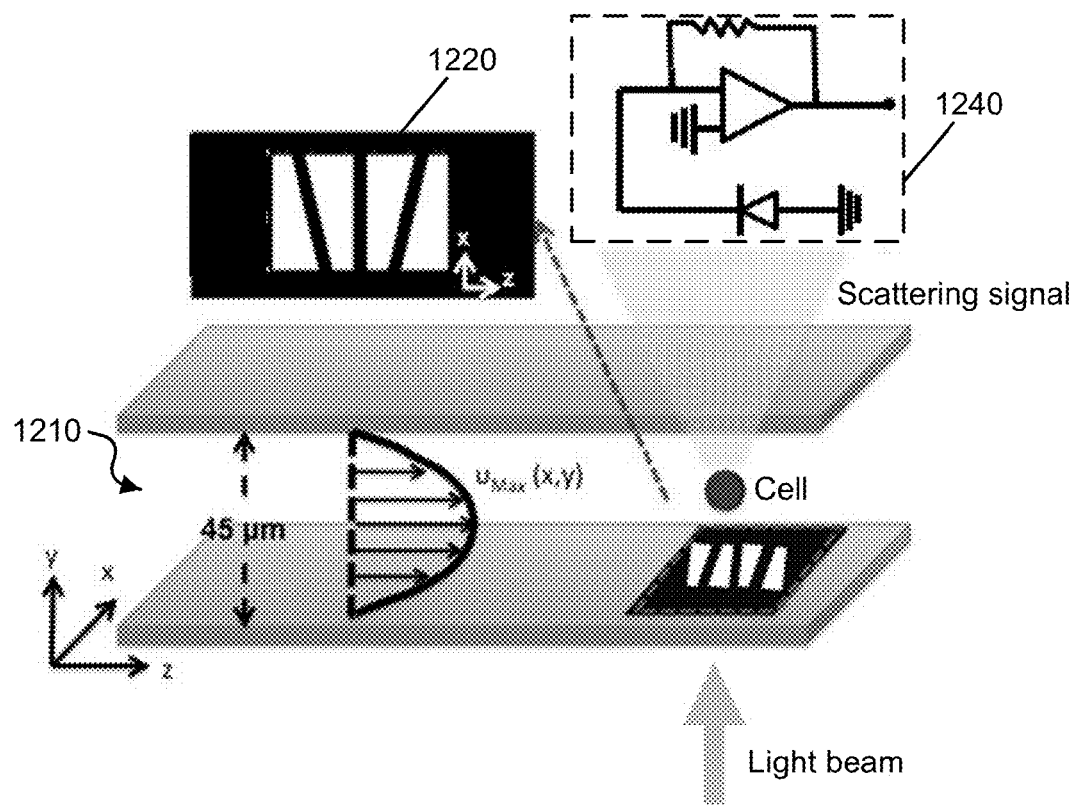
FIG. 12A shows a schematic diagram of a microfluidic channel of an exemplary optofluidic device of the disclosed technology.

FIG. 12A shows a schematic diagram of a microfluidic channel 1210 of an exemplary optofluidic device of the disclosed technology. For example, the microfluidic channel 1210 includes a mask 1220 located on the surface, in which the mask 1220 includes a pattern of openings to form a sample interrogation area. The optofluidic device can generate and transmit a probe beam that is filtered through the pattern of openings of the mask 1220 as it enters the microfluidic channel 1210. Upon passing through the mask 1220, the probe beam is spatially modulated by the mask 1210 to carry the spatial pattern. This spatially modulated probe beam interacts with the particles inside the channel to produce output filtered light which is received by a photodetector 1240 (e.g., silicon (Si) PIN photoreceiver) located on the opposite end of the optofluidic device from the source of light. Samples including living cells can be deployed in the optofluidic device to flow through the microfluidic channel 1210. For example, scattering signals can be produced by the cells scattering the filtered light passing through the mask 1220 that exhibit distinct waveforms in time domain. The waveforms can be detected by the photodetector 1240 that interfaces with a processing system that can determine the positions and velocities of these cells in the microfluidic channel.

For example, the microfluidic channel 1210 and the mask 1220 can include configurations like that of the microfluidic channel 110 and the mask 120 shown in FIGS. 1A and 1B. For example, the exemplary channel can be configured to be 5 μm long (e.g., as shown in FIG. 12A in the z-direction) and have a rectangular cross section with a width of 100 μm (e.g., x-direction) and a height of 45 μm (e.g., y-direction). For example, the mask 1220 can be placed at 4.5 cm from the inlet of the microfluidic channel 1210. For example, the pattern of openings of the exemplary mask 1220 can include a pattern of four trapezoidal slits, e.g., in which each exemplary trapezoidal slit includes base lengths of 100 μm and 50 μm arranged in an alternating pattern with a separation of 50 μm, with a total pattern length of 450 μm. The exemplary four-slit mask can be formed by Ti/Au (100 nm/200 nm) metal layers deposited on a glass substrate using standard E-beam evaporation and metal lift-off process.

Figure 12B:
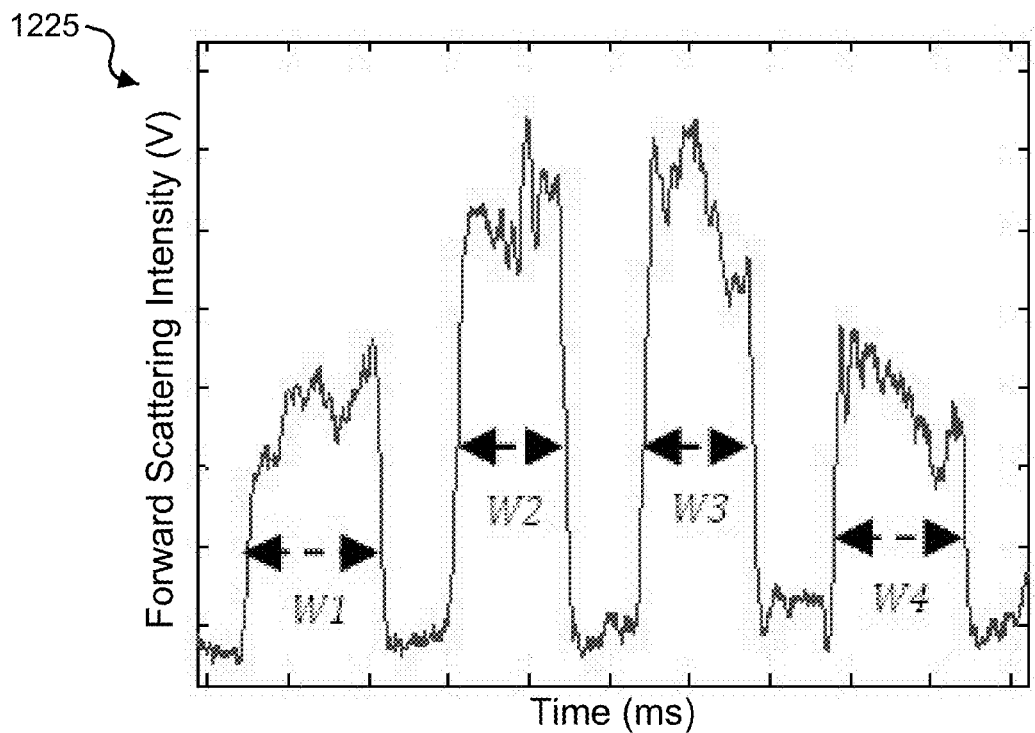
FIG. 12B shows a plot of a waveform based on an exemplary spatial pattern for optical coding.
Figure 13A:
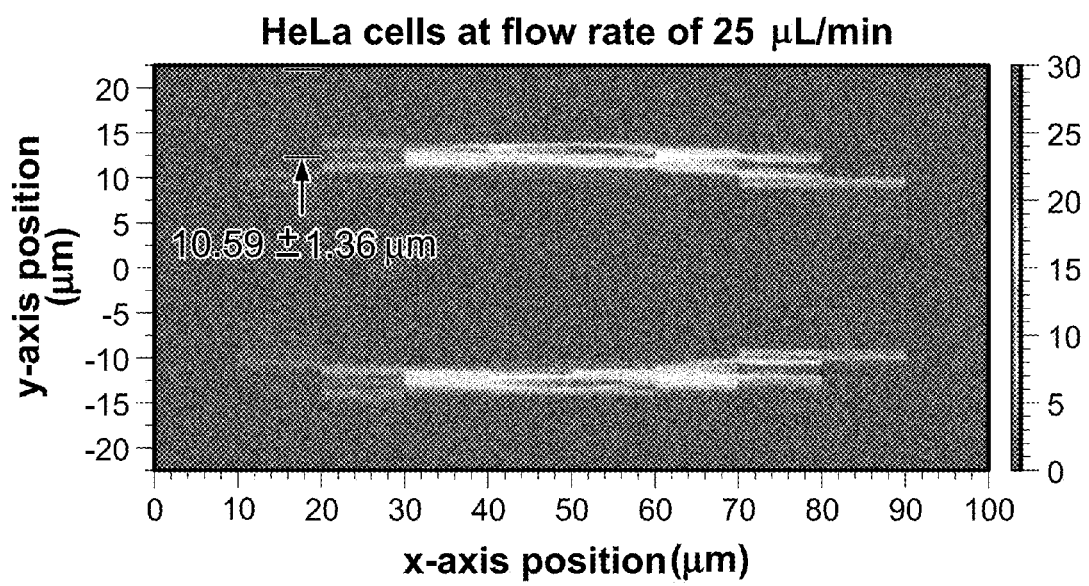
FIGS. 13A-13F show data plots of the population distribution of HeLa cells and RBCs over the cross section of an exemplary microfluidic channel.
Figure 13B:
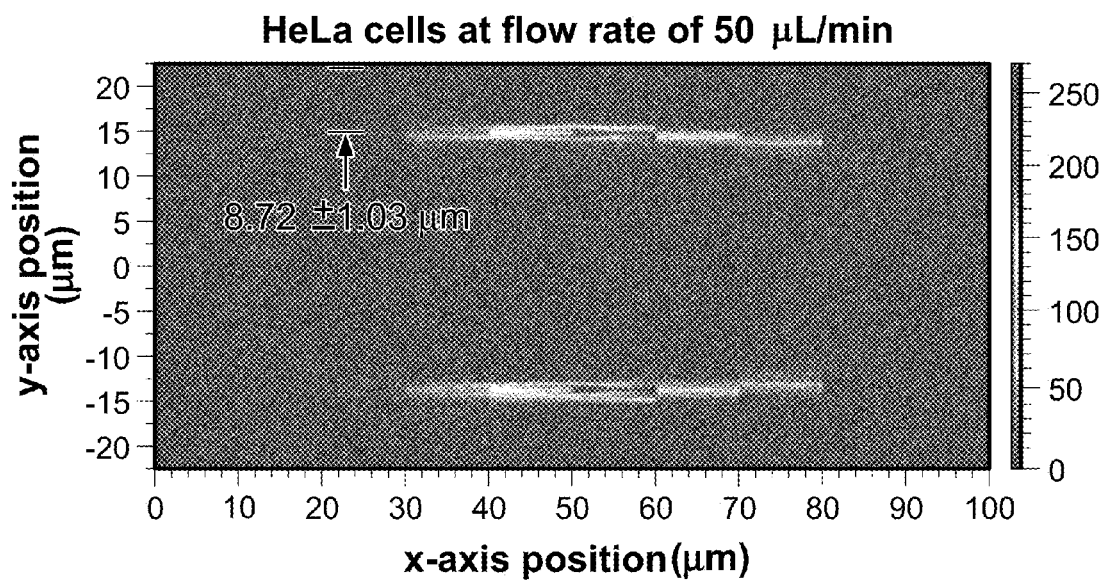
Figure 13C:
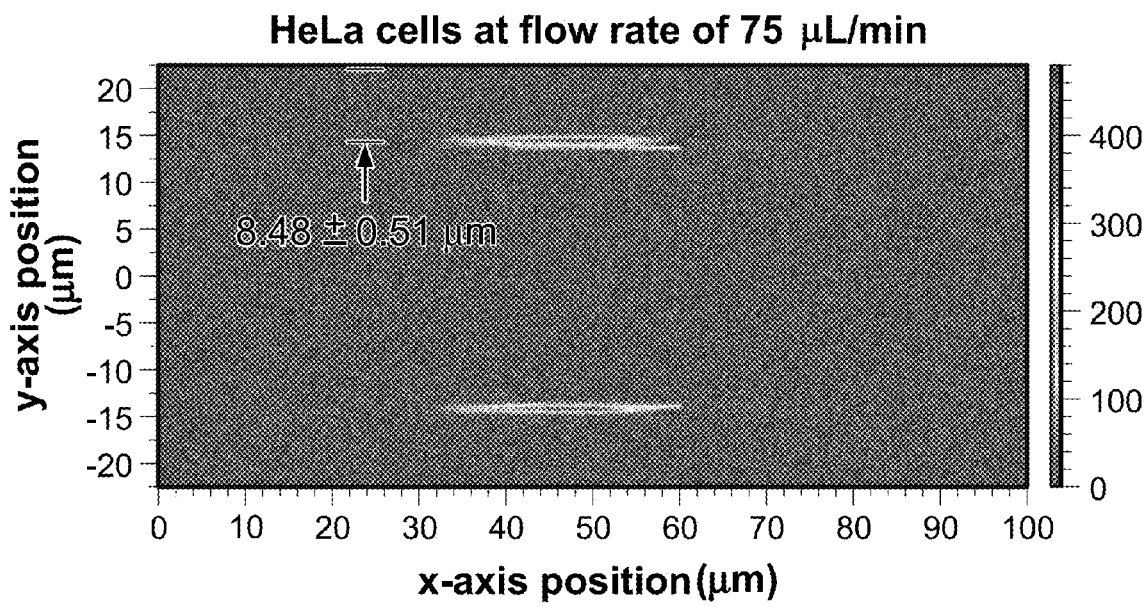
Figure 13D:
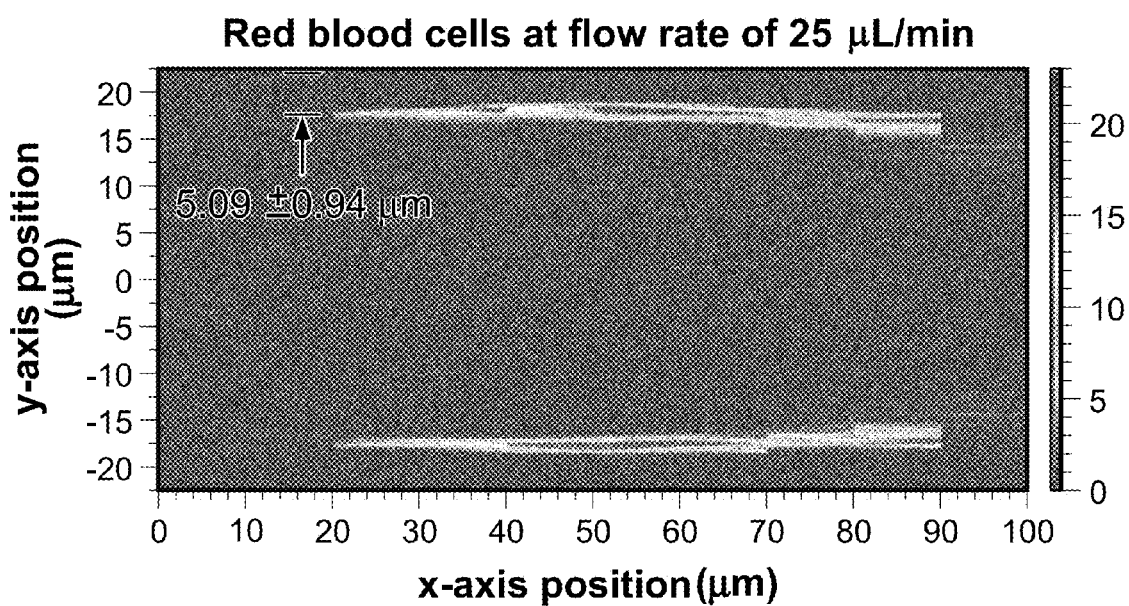
Figure 13E:
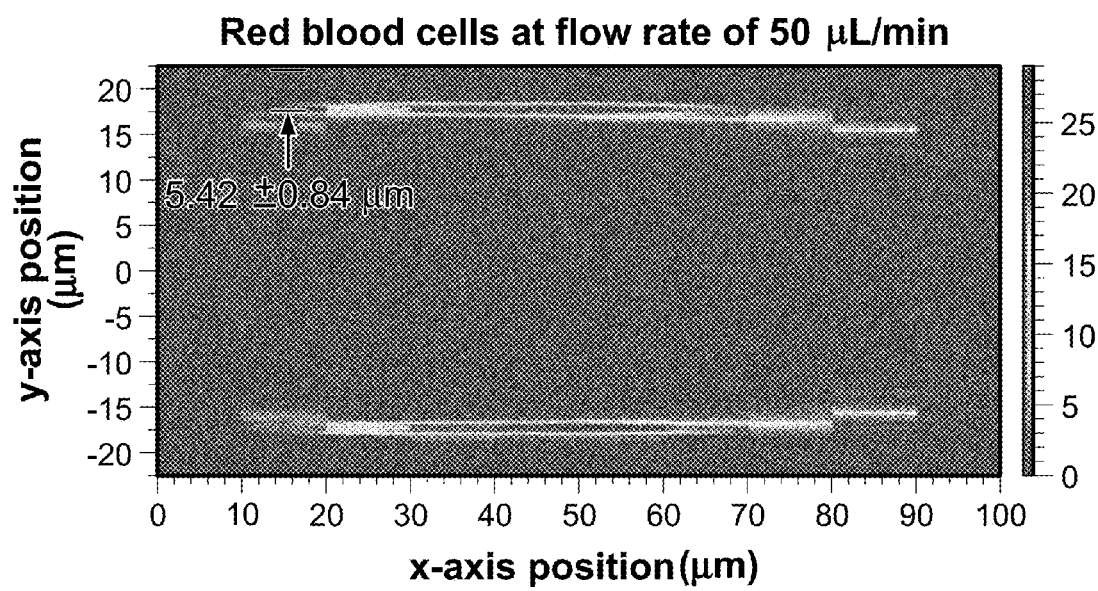
Figure 13F:
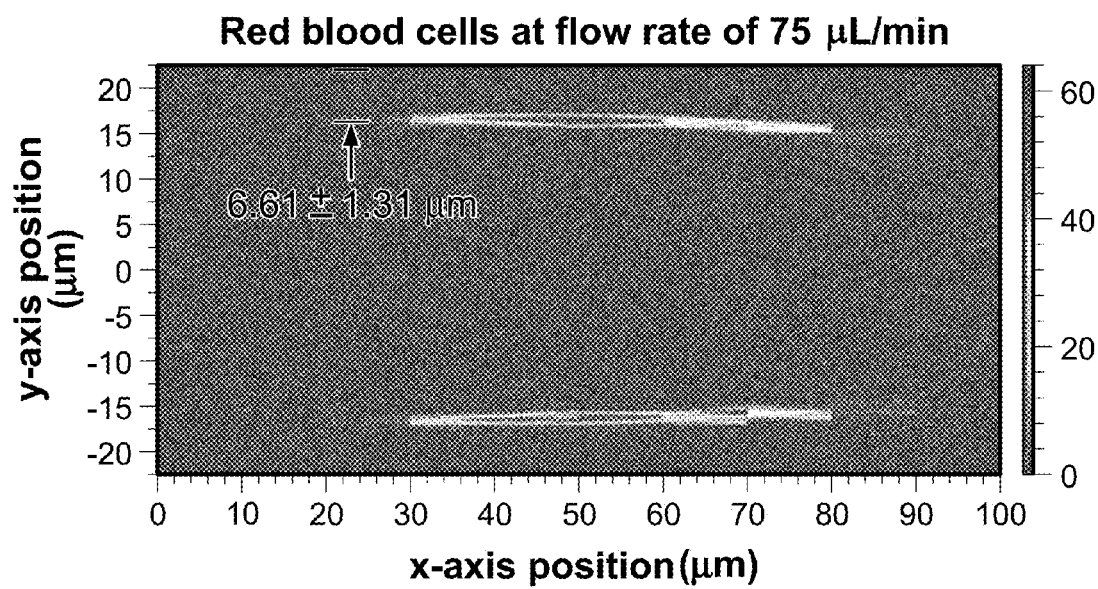

An exemplary forward scattering signal of each cell passing through the exemplary spatial pattern of the mask 1220 exhibits a specific waveform according to the lateral position through which the cell travels, as illustrated by the waveform plot 1225 in FIG. 12B. For example, a representative forward-scattering signal is shown in the plot 1225 corresponding to a cell traveling through different lateral positions of the microfluidic channel 1210. Depending on the trajectory of moving samples, the forward scattering signals can be encoded by the spatial mask and exhibited distinct waveforms in time domain. The waveforms can be used to obtain the positions of these cells in the microfluidic channel. The exemplary detected intensity-modulated FS signal (e.g., modulated by the exemplary trapezoidal slits of the mask 1220) displays four peaks, e.g., W1, W2, W3, and W4, corresponding to the four sequential trapezoidal slits. For example, the ratio between the width of the first peak (W1) and the second peak (W2) yields information about the cell position in the x-axis. The same information can also be obtained from the ratio of W4 and W3. The redundancy helps reduce noise and improve measurement accuracy. The velocity of the cell can be acquired by dividing the total pattern length by the duration of signal. For example, knowing the position in the x-axis and the velocity, the cell position in the y-axis can be obtained using the property of laminar flow that gives rise to a parabolic velocity profile represented in Eq. (1).

The knowledge of both the position and speed of each cell can provide information about the property of cells. For example, when the ratio between the particle diameter and the channel dimension is greater than 0.07, the inertial effect can focus the particles toward equilibrium positions inside the channel. In addition, for example, if similar sized cells have different stiffness, the more deformable cells tend to migrate laterally toward the central area in the x-axis.

The exemplary optofluidic device of FIG. 12A can be fabricated using PDMS (e.g., Sylgard 184, Dow Corning, Mich.) soft lithography process. For example, after curing the PDMS, a PDMS film can be separated from the silicon mold master. Holes for inlet and outlet can be punched through the PDMS replica. On a separate glass slide, a Ti/Au film (e.g., 100/200 nm in thickness) can be deposited and lithographically patterned to form a spatial mask. For example, the PDMS film patterned with the microfluidic channel and inlet and outlet can be bonded to the glass slide with oxygen plasma treatments of the PDMS surface. For example, an alignment apparatus can be used to assure good alignment between the Ti/Au patterns on the glass slide and the microfluidic cannel. In some implementations, for example, a semiconductor diode laser can be used as the light source and a silicon PIN photoreceiver can be used to detect FS signals. The exemplary optofluidic device can include a syringe pump (e.g., Harvard Apparatus, Pump Elite 11) can be used to inject samples to the device at designed flow rates. For example, after the measurements of forward scattering signals, a signal processing algorithm of the disclosed technology (e.g., implemented in MATLAB) can be used to remove noise and extract events.

Exemplary implementations of the disclosed optofluidic device were performed for device characterization with selected cell types, e.g., including samples with cancer cells (HeLa cells), red blood cells (RBCs), and white blood cells (WBCs). For example, HeLa (human cervical epithelioid carcinoma) cells were cultured in the growth medium in a humidified incubator at 37° C. in 5% $CO_2$ and then fixed with paraformaldehyde prior to the implementations using the exemplary optofluidic device. For example, to prepare WBC samples, whole blood was lysed with commercial lysing buffer (eBioscience, Calif.). For example, to prepare RBC samples, 100 μL of whole blood was centrifuged at 10,000 rpm. 5 μL of red blood cells (RBCs) was carefully taken out from the bottom of canonical tubes (e.g., below the buffy coat) and then diluted 2 million times using a buffer solution. The buffer solution used for sample dilution included 10 mM ethylenediaminetetraacetic acid (EDTA), 1% bovine serum albumin (BSA), and 1× phosphate buffered saline (PBS). For example, for neutrophil counting tests, whole blood samples were taken from human volunteers using a finger prick. A blood drop was diluted 300 times with 1 mL of buffer solution, followed by adding 450 μL lysing agent. After keeping the sample in the ambient environment for 10 minutes, the blood mixed with lysing agent was introduced into the exemplary optofluidic device for measurement without further preparation. For example, to characterize the exemplary device and test the operation principle in the described implementation, only one cell type at a time before testing samples with mixed cell types.

Signals from HeLa cells were first characterized using the space-time optically encoded signal from the exemplary lab-on-a-chip optofluidic device. The exemplary implementations included testing HeLa cells at three different flow rates of 25 μL/min, 50 μL/min and 75 μL/min. The dimensions of the exemplary optofluidic device produce a microchannel hydraulic diameter (e.g., $D_h = (2w \times h)/(w+h)$) of 62.1 μm, where w and h represent the width and height of the channel. Under the average flow velocities of 9, 18 and 27 cm/s for the corresponding flow rates of 25, 50, and 75 μL/min, the Reynolds number (Re) was calculated to be 5.59, 11.18 and 16.77, respectively. More than 500 cells were detected within a measurement period of 90 seconds, and the encoded FS signals were processed using the disclosed algorithms implemented in Matlab. For example, the signals first pass a high pass filter and a low pass filter to remove noise and baseline drift. Then an exemplary peak detection algorithm based on predefined threshold was applied to register each event. The exemplary implementations included the use of COMSOL simulation to retrieve the maximum velocity of flow at each flow rate, e.g., in which the spatial distribution of cells was obtained using the described method.

FIGS. 13A-13F show data plots of the population distribution of HeLa cells and RBCs over the cross section (100 μm×45 μm) of the microfluidic channel at flow rates of 25, 50, and 75 μL/min (from left to right). When the flow rate increases, HeLa cells migrate toward the center of the microchannel along the x-axis. For example, detailed analyses on the HeLa cell distribution along the x-axis show a standard deviation ($\sigma_x$) of 17.26 μm, 12.89 μm and 7.59 μm at the flow rates of 25, 50, and 75 μL/min, respectively. HeLa cells were tightly focused to narrow positions in the y-axis. For example, at the flow rates of 25, 50, and 75 μL/min, the standard deviation ($\sigma_y$) of each band in the channel height direction is as small as 1.36 μm, 1.03 μm, and 0.51 μm, respectively. Given the ~20 μm average size of HeLa cells, this represents an extremely tight distribution along the y-axis. In addition, the position of the peak population of HeLa cells moves closer to the channel wall with increasing flow rates. The very tight population distribution represents steep energy minima. The exemplary resultant data demonstrates the effect of cell stiffness on the cell distribution in a microfluidic channel. Like most cancer cells that have the tendency to migrate through tissue barriers to enter the blood vessel to metastasize, HeLa cells are more deformable than most normal cells such as red blood cells. Comparing the distributions of HeLa cells and red blood cells using the exemplary optofluidic device, the larger and softer HeLa cells can be clearly distinguished from the red blood cells from their positions in the y-axis.

Figure 14A:
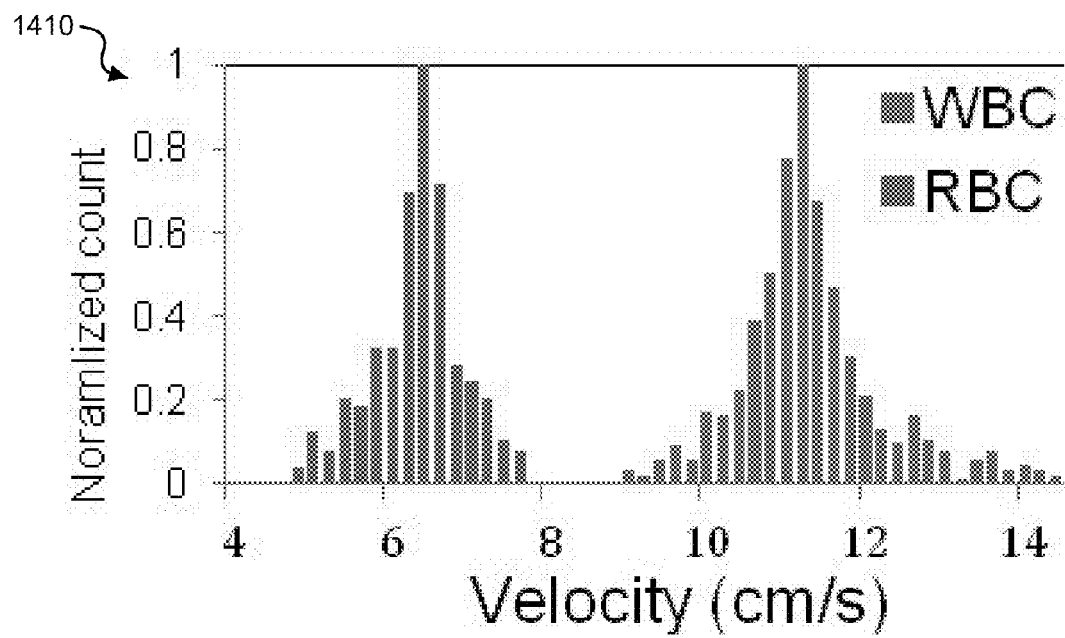
FIG. 14A shows a histogram of WBCs and RBCs distinguished by an exemplary optofluidic device using cell velocity as the parameter.
Figure 14B:
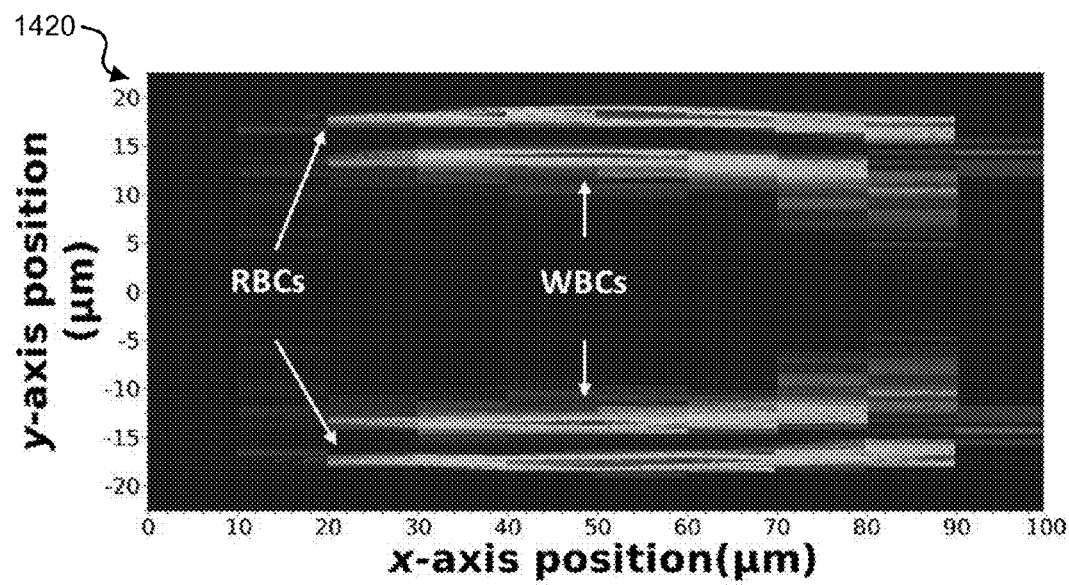
FIG. 14B shows data plot of the population distributions for WBCs and RBCs over the cross section of an exemplary microfluidic channel.

Exemplary implementations using the optofluidic device of the disclosed technology were performed to classify white blood cells and red blood cells. For example, the separation of white blood cells from red blood cells can be a clinically relevant test of immune functions. For example, after dilution of the RBC-lysed whole blood to a WBC concentration of around 100 counts/μL, WBCs were introduced into the device at a flow rate of 25 μL/min. To test the RBCs, whole blood was diluted by 2 million times and introduced into the device at the same flow rate of 25 μL/min. A minimum of 1,500 encoded FS signals from each cell type were detected and analyzed to create the population distribution plots. The exemplary samples of RBCs and WBCs were tested separately. FIG. 14A shows a histogram 1410 of WBCs and RBCs distinguished by an exemplary optofluidic device using cell velocity as the parameter. FIG. 14B shows data plot 1420 of the population distributions for WBCs and RBCs over the cross section of an exemplary microfluidic channel. As shown in FIGS. 14A and 14B, two distinctive regimes for WBCs and RBCs are present (FIG. 14A), and the separation is primarily along the y-axis (FIG. 14B). As shown in the data plot 1420, RBCs were determined to be mostly populated at a distance of 17.41 μm from the center of the channel in the y-axis, e.g., with $\sigma_y$ being 0.94 μm. In contrast, for example, larger WBCs were determined to be mostly populated at a distance of 12.57 μm from the centerline, with $\sigma_y$ being 1.80 μm. For example, "gating" can be defined in the x-y plane in a similar fashion to user-defined gating with a conventional flow cytometer, and thus the separation between RBCs and WBCs can be even more distinctive and accurate than the single parameter plot shown in the data plot 1410.

Exemplary implementations using the optofluidic device of the disclosed technology were performed to count neutrophil cells from whole blood samples. For example, cell size and stiffness can be used as biomarkers that can be faithfully represented in the population distribution plot. The neutrophil count can reveal the condition of the immune function and has been used as a key parameter for drug dosage and cytotoxicity in chemotherapy. For example, to reduce the chance of hospital infection and cost, it is desirable to perform neutrophil test at point-of-care clinics or at patient's residence in a self-administered fashion. For example, the feasibility of counting neutrophil population was investigated from a very small amount (e.g., 3-5 μL) of whole blood with minimum sample processing steps. Without adding any anticoagulation agent, the blood sample was diluted in a buffer solution to a total volume of 1 mL with RBC lysing agent. The RBC-lysed diluted blood was directly introduced to the exemplary optofluidic device for testing without centrifuge and pipetting.

Within the WBC family, there exists a diverse size distribution among different subpopulations of WBCs, e.g., lymphocytes being 7.5 μm, monocytes being 9.1 μm, and neutrophils being 8.2-8.4 μm. WBCs can form a continuum in their size distribution, e.g., which can make cell classification by size alone very difficult without expensive flow cytometers that can give out very low intrinsic values of coefficients of variation (CVs). For example, since the disclosed method can be implemented to measure cell positions within the channel and the cell positions depend strongly on cell stiffness, the disclosed technology can be used to count neutrophils from other types of WBCs, e.g., such as lymphocytes and monocytes, because of the high deformability of neutrophils. For example, being of similar size, neutrophils are more than twice as deformable as monocytes, and the stiffness of lymphocytes is between that of neutrophils and monocytes.

Figure 15A:
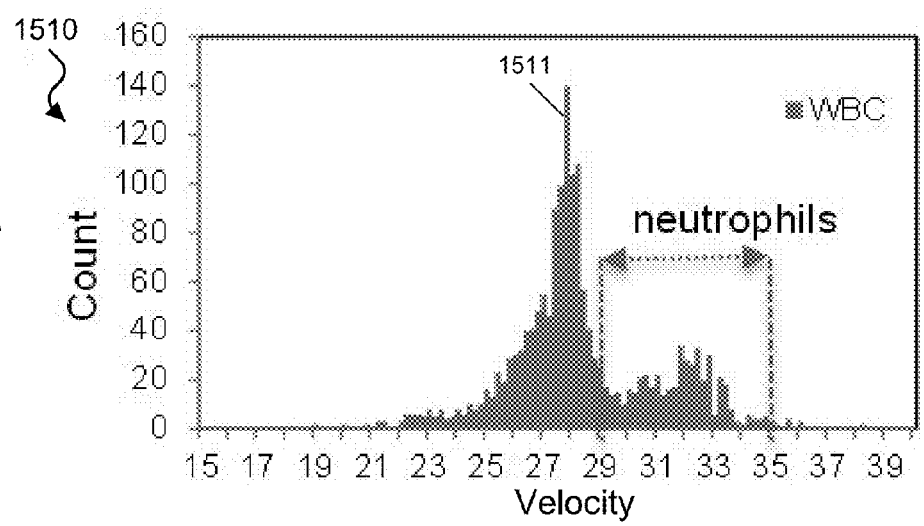
FIG. 15A shows a velocity histogram of white blood cells from a red blood cell-lysed whole blood sample using an exemplary optofluidic device.

FIG. 15A shows a velocity histogram 1510 of white blood cells from a 3 μL RBC-lysed whole blood sample using an exemplary optofluidic device at a flow rate of 75 μL/min. The histogram 1510 shows a distinguishable population of neutrophils from other WBCs, e.g., which can be attributed to the high deformability of neutrophil cells. The exemplary peak (e.g., peak 1511), found to the left of the neutrophil in the histogram 1510, represents signal from other WBC types plus RBC residues, e.g., since the sample did not go through centrifuge.

Figure 15B:
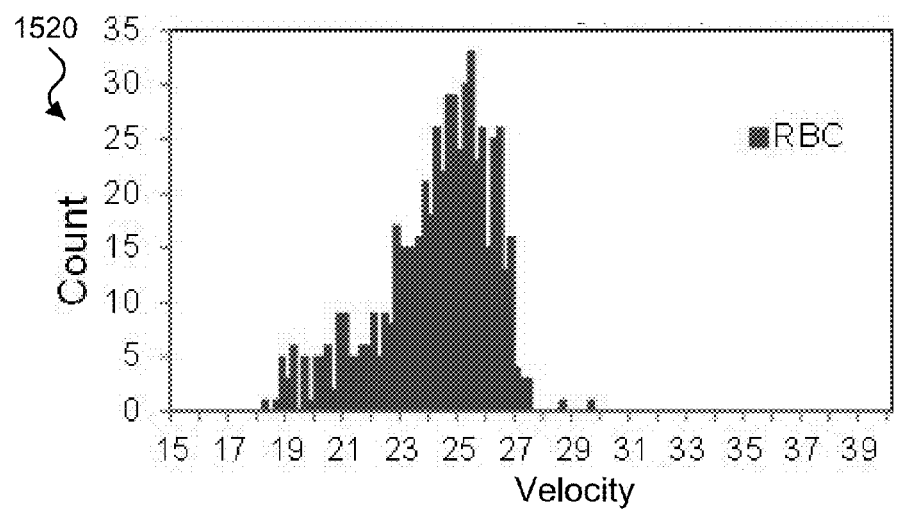
FIG. 15B shows a velocity histogram of red blood cells using an exemplary optofluidic device.

The analysis that RBC residues are found in the lower velocity group is supported by the RBC histogram of FIG. 15B, obtained from an unlysed diluted whole blood test at the same flow rate as that in the WBC histogram. FIG. 15B shows a velocity histogram 1520 of red blood cells using an exemplary optofluidic device at a flow rate of 75 μL/min.

Figure 15C:
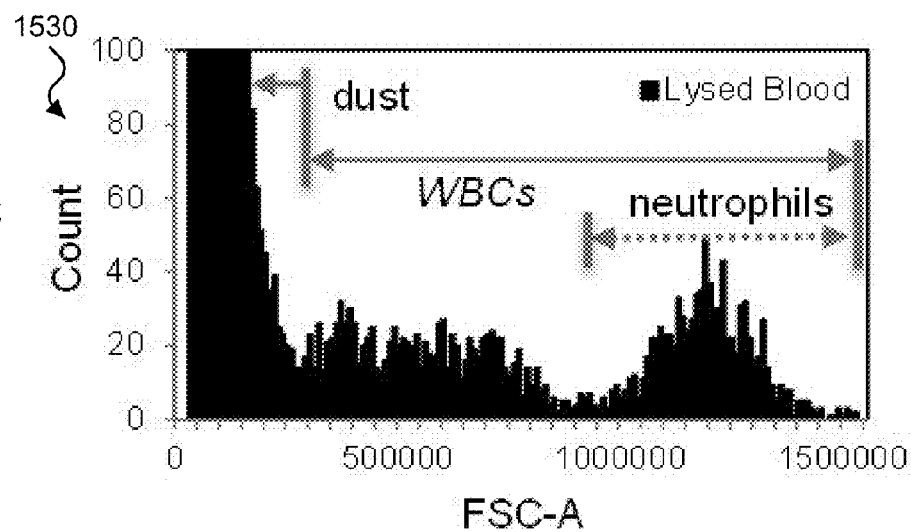
FIG. 15C shows a histogram of lysed, centrifuged whole blood measured with a conventional flow cytometer.

To further verify the results, an implementation of a conventional flow cytometer was performed using a standard blood preparation protocol, e.g., including the multiple steps of anticoagulation, RBC lysing, centrifuge, and pipetting. FIG. 15C shows a histogram 1530 of lysed, centrifuged whole blood measured with a conventional flow cytometer (e.g., Accuri C6). The horizontal solid line in the histogram 1530 indicates the total WBC count, and the horizontal dash line in the histogram 1530 indicates the neutrophil population. The population of neutrophils was shown to be ~55% of the total WBC population. In contrast, for example, the optofluidic device of the disclosed technology showed the percentage of neutrophils to be about 30% of the total detected cell population, as shown in the histogram 1510. The discrepancy between the detection of neutrophils between the exemplary optofluidic device and the conventional flow cytometer can be attributed to RBC residues in the sample, which can be distinguished using the optofluidic device of the disclosed technology.

Figure 15D:
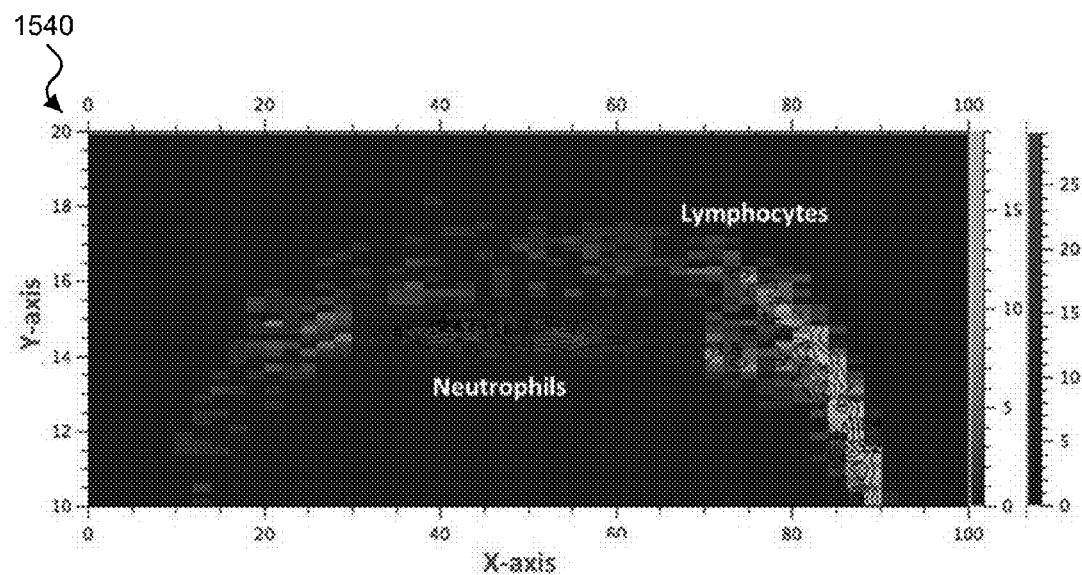
FIG. 15D shows a distribution plot for neutrophils and lymphocytes from the WBCs sample over the cross section of an exemplary microfluidic channel.

FIG. 15D shows a distribution plot 1540 for neutrophils and lymphocytes from the WBCs sample. For example, due to the larger size and higher deformability of neutrophils as compared to lymphocytes, two separate clusters of WBCs can be observed. For example, the neutrophil cells were more concentrated around the center (x-axis) and farther away from the channel wall (y-axis). This distinct feature can allow users to define the gating, e.g., as indicated by red and green color regimes, to count cells (e.g., neutrophils).

The exemplary optofluidic lab-on-a-chip device was shown to successfully measure acquire the position and velocity of each cell in the flow and generate 2-D cell distribution plots over the cross section of the channel by optically encoded forward scattering signals. For example, the cell distribution within the microfluidic channel of an exemplary optofluidic lab-on-a-chip device was shown to be highly sensitive to cell size and stiffness. The exemplary optofluidic lab-on-a-chip device was implemented in an application of neutrophil cell detection and counting in a whole blood sample with a simplified blood preparation process, e.g., skipping the steps of anticoagulation, centrifuge, anti-body labeling or staining, filtering, etc.

Figure 16:
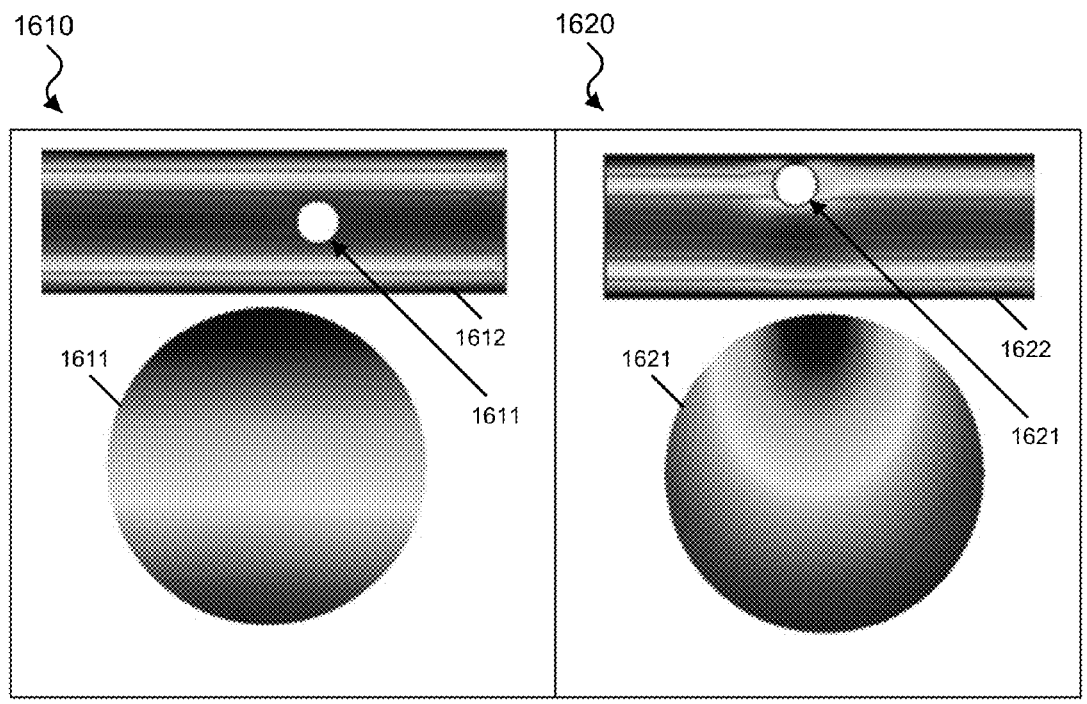
FIG. 16 shows color-coded shear stress distribution plots of a spherical particle in an exemplary microfluidic channel at different positions inside the channel.

Exemplary fluid dynamic simulation were implemented to further demonstrate the sensitivity of cell positions to cell mechanical and geometric properties, e.g., producing insight on the capabilities and performance of the disclosed technique for cell counting and other biomedical applications. FIG. 16 shows a color-coded shear stress distribution plot 1610 of a spherical particle 1611 in a microfluidic channel 1612 when the object is at a central position inside the channel 1612. FIG. 16 also shows a color-coded shear stress distribution plot 1620 of a spherical particle 1621 in a microfluidic channel 1622 when the object is at a position near the edge of the channel 1622. In both plots 1610 and 1620 of FIG. 16, the dark blue and dark red colors represent high magnitudes of shear stress of opposite signs, and the light green and yellow colors represents low shear stress regions. For example, the particle experiences a focused stress point when it is near the channel wall as compared to the central region of the channel. The plots 1610 and 1620 show the shear stress distribution of a rigid spherical particle traveling near the center (plot 1610) and edge (plot 1620) of the microfluidic channel.

The disclosed technology includes techniques to measure the velocity and position of each particle or sample traveling through a microfluidic channel, which can produce valuable information for the design and assessment of lab-on-a-chip devices, such as flow cytometers and complete blood count devices, and point-of-care diagnostics. For example, in the United States each year there are 1.3 million newly diagnosed cancer patients and around 650,000 patients with recurrent cancer tumors, amounting to about 2 million cancer patients being treated each year. Among them about 50% or 1 million cancer patients receive chemotherapy. Neutropenia is a common side effect of chemotherapy, characterized by an abnormally low number of neutrophils which usually make up 50-70% of circulating white blood cells and serve as the primary defense against infections. For example, without prompt medical attention, the condition of neutropenia may become life-threatening (e.g., neutropenic sepsis). Since the majority of oncology patients are treated on an outpatient basis, the number of neutrophils should be closely and frequently monitored to allow timely administration of granulocyte-macrophage colony-stimulating factor (GM-CSF) to raise white blood cell counts in the event of severe neutropenia. For example, if chemotherapy patients develop fever after regular clinic hours, they should be immediately sent to the emergency room/urgent care to check their WBCs to exclude neutropenia. Currently, in common practice, for example, patients in their first year of chemotherapy may need to make 10 to 24 physician visits, e.g., not counting hospitalizations to perform neutrophil counting. This can require tremendous amounts of healthcare resources, add to patient's pain and inconvenience, and cause very high risks of nosocomial infections. Nosocomial infections are infections resulting from treatments in a hospital or healthcare environment. For example, patients undergoing antiproliferative chemotherapy with neutropenia are particularly sensitive to nosocomial infections. For example, the Center for Disease Control (CDC) estimates 1.7 million hospital-associated bacteria infections in the US, e.g., causing or contributing to 99,000 deaths each year. Since 2008, when the Centers for Medicaid Services (CMS) declared they no longer reimburse hospitals for any hospital acquired infection, US hospitals have been plagued with the out of pocket expense of hospital acquired infections, amounting to $40 billion dollars a year.

The disclosed optofluidic technology can be implemented to address this important unmet need for self-administered neutrophil counting and characterization (e.g., characteristic cell volume and deformability) among other blood cells. The present optofluidic technology can include the following salient features, such as minimal invasiveness requiring only 5 µL of blood (e.g., similar amount to glucose test), straightforward sample preparation and test procedures that can be performed by persons without medical training, accurate test results that are easy to understand and compliant to medical standards, and low equipment cost and compactness. For example, under a given channel geometry and flow conditions, the combined information of cell size, shape, and deformability can be used to determine the stable positions of cells in the channel due to the fluidic dynamic properties. Therefore, precise measurements of cell positions inside the microfluidic channel yield unambiguous signatures for cell types, which can be provided by an exemplary optofluidic lab-on-a-chip device, e.g., by using an encoded optical forward scattering signal.

In one example of a point-of-care, self-administered neutrophil characterization technique using an exemplary optofluidic lab-on-a-chip device, the patient can take a 5 µL sample of blood (e.g., in the same manner as glucose test for diabetic patients) and dilute the blood in 1 mL buffer with red blood cell lysing agent. Cumbersome steps may impede self-administered test, such as centrifugation, addition of anticoagulation agents, antibody labeling, filtering, and pipetting are eliminated from the exemplary process. The described optofluidic lab-on-a-chip device design can exclude any expensive and fragile parts, e.g., such as high-end lasers, photomultiplier tubes (PMTs), sophisticated optics, and flow control systems to form sheath flow. For example, the cell classification processing techniques can be developed in the form of algorithms or computer programs that can be downloaded from the Internet, e.g., allowing patients to obtain data that are easy to understand and compliant to the medical standards. The entire procedure, including sample preparation, testing, and data analysis, can be implemented in less than 20 minutes, and the process that involves user actions is minimal.

For example, implementation of the exemplary point-of-care, self-administered optofluidic lab-on-a-chip device can provide benefits to cancer patients, e.g., because the device can greatly reduce the risk of hospital infection, save the high healthcare costs associated with nosocomial infections, improve outcomes for chemotherapy due to close monitoring of the side effect of neutropenia, and minimize the inconvenience and pain for unnecessary hospital and emergency room visits. Additionally, for example, the present technology can be applied in other applications that benefit from self-administered blood testing, e.g., such as detection of blood cells in urine for nearly 400,000 end stage renal disease (ESRD) patients that are on peritoneal dialysis (PD), among many other examples.

For example, an exemplary point-of-care microfluidic device of the disclosed technology that can be self-administered can include a microfluidic channel structured to carry a fluid sample containing particles along a direction from an inlet region to an outlet region, the microfluidic channel including a pattern of openings spatially arranged on a surface of the channel, in which at least two openings of the pattern of openings have unequal widths along the direction, a light source that generates a light beam through the pattern of openings to illuminate the fluid sample, in which each particle scatters the light beam to produce an optical scattering signal at each position that the particle flows along the pattern of openings of the microfluidic channel, an optical detector arranged in a location relative to the pattern of openings to receive the optical scattering signal and produce a scattering signal waveform, the waveform including a signal peak corresponding to each opening of the pattern of openings, and a data processing and storage unit communicatively coupled to the optical detector, the data processing and storage unit to convert the scattering signal waveform from an analog signal format to a digital signal representation and to store the digital signal representation in a data storage. Also, for example, the exemplary microfluidic device can further include an input/output (I/O) unit communicatively coupled to the data processing and storage unit to interface with an external computer system that can retrieve the digital signal representation from the data storage to the external computer system. For example, the external computer system can include a personal computer, tablet, or smartphone device.

In another aspect, the disclosed technology includes techniques for the classification of cells using a minimal number of parameters (e.g., FS intensity and LAS or SS intensity) to establish a classifier that divides all components into several well-defined groups. For example, in most cases, a classifier with a clear boundary does not inherently exist to separate one group from another, especially in the biological world. One method for classifying these conditions is to enhance dimensions of sample points. For example, one can expand those inseparable cases into a higher-dimensional feature space. Given the appropriate expression information to build the multi-dimensional feature space, the hyperplane for separation may be achieved.

Figure 17A:
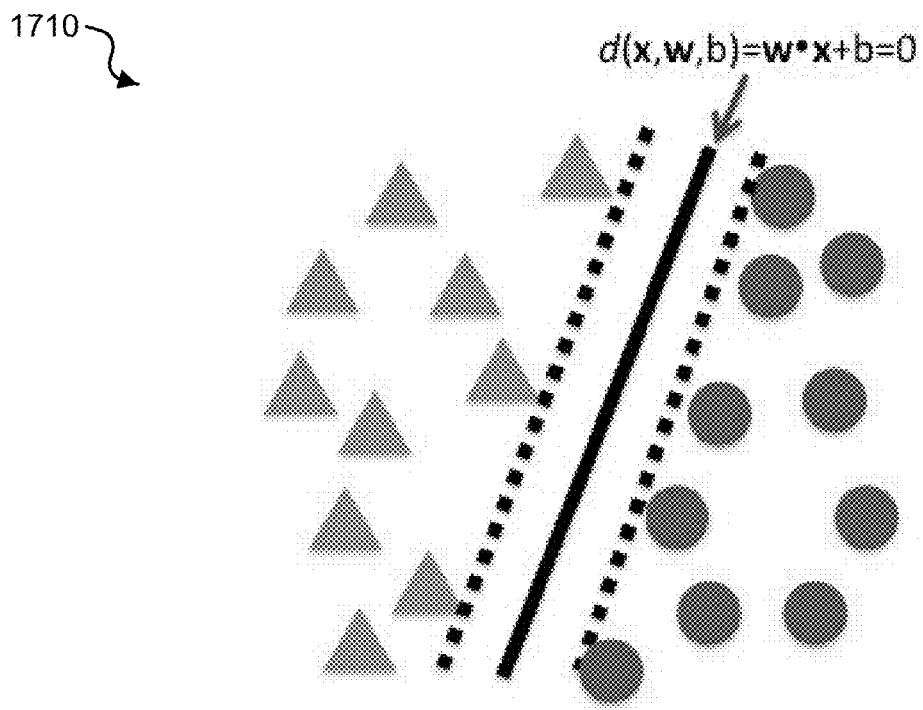
FIGS. 17A and 17B show plots that demonstrate exemplary techniques for data classification by using support vector machine algorithms.

The disclosed technology includes algorithms of support vector machine (SVM) to create a classifier with a maximal margin for the separating hyperplane that can effectively recognize each group (e.g., of cells), as well as avoid overfitting. FIG. 17A shows a plot 1710 that demonstrates one simple technique for the classification by using a linear separating hyperplane. For example, the plot 1710 includes data points representing different groups of data (e.g., triangle data points and circle data points). To determine the exemplary linear separating hyperplane, one can assume an expression vector x for each event, in which SVMs would have a decision function $d(x,w,b)=w \cdot x+b$, e.g., where • means dot product, w is the normal vector to the hyperplane and b is a scalar called bias factor. Because the output of $d(x,w,b)$ is a value, the indicator function, F, is defined as sign of $d(x,w,b)$ that indicates the classification for each event. The optimal canonical hyperplane can occur when the decision function equals to zero, e.g., $d(x,w,b)=w \cdot x+b=0$, and the separating margin, $\gamma$, for both sides from the hyperplane is maximal, e.g., $$2\gamma = \frac{2}{\|w\|}.$$

For example, after the complete training step, given a set of unknown expression vector $x_N$, SVM is able to produce an output for $d(x_N,w,b)$. Thus, for example, if F of $d(x_N,w,b)$ is negative, the event belongs to type 1; on the other hand, the event is classified into type 2 when F of $d(x_N,w,b)$ is positive.

Figure 17B:
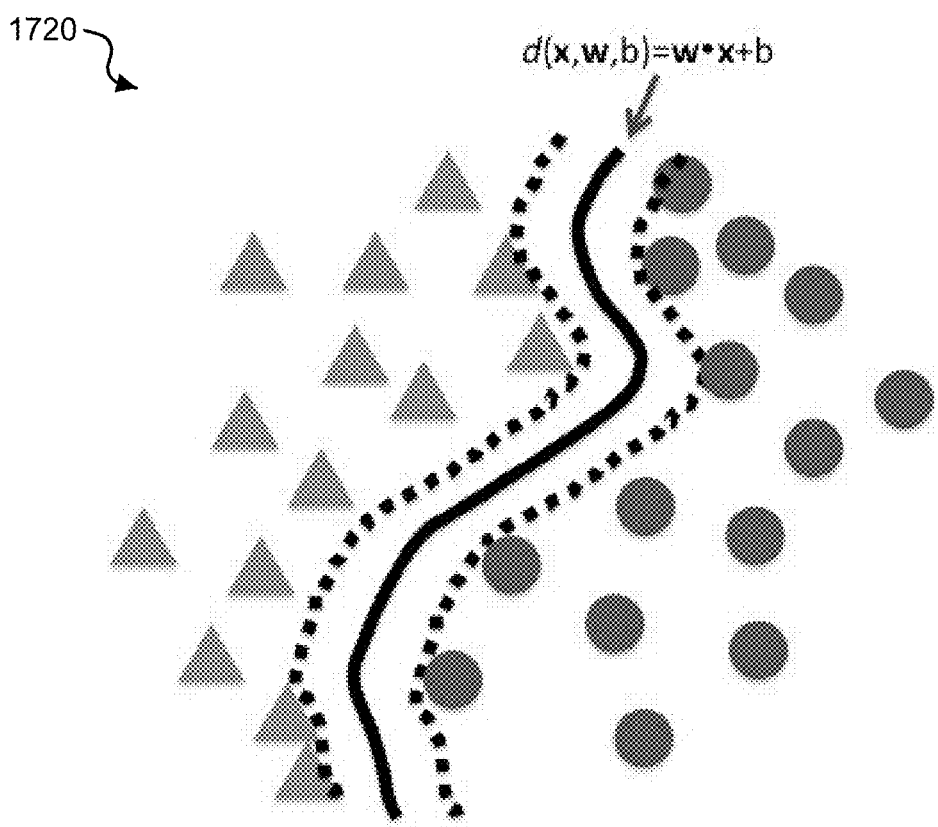

However, in some situations, data sets might not be classified linearly because of the mislabelled events in the database or inappropriate classifiers used. For example, the former issue of mislabeled events can be addressed by introducing the soft margin that allows some data points to be arranged into wrong side of the hyperplane. For the latter problem of inappropriate classifiers used, a nonlinear classifier can be applied, as illustrated in FIG. 17B. FIG. 17B shows a plot 1720 of data points representing different groups of data (e.g., triangle data points and circle data points) in which an adequate kernel function, $K(x_i, x_j)$, can be used to maximize the separating margin. For example, since SVM algorithm was originally based on a linear learning machine technique, introducing a nonlinear kernel function can be a functional tool to address this purpose without changing the fundamental of computation algorithms. To use nonlinear kernel functions, the previous dot product of decision function can be substituted with designed kernel functions that enable the algorithms of SVMs to achieve the maximum-margin hyperplane in a high-dimensional feature space. For example, the kernel functions can exist with various forms such as polynomial, hyperbolic tanget, inverse multiquaric and Gaussian radial basis function (RBF). The disclosed technology can include the use of kernel functions in which the results are conducted with Gaussian RBF in the form of $K(x_i, x_j)=\exp(-\gamma\|x_i-x_j\|^2)$, e.g., because it has less number of hyperparameters that affect the complexity of model selection and usually allows to obtain higher accuracy for the present examples (e.g., such as distinguishing groups of cells).

Figure 18A:
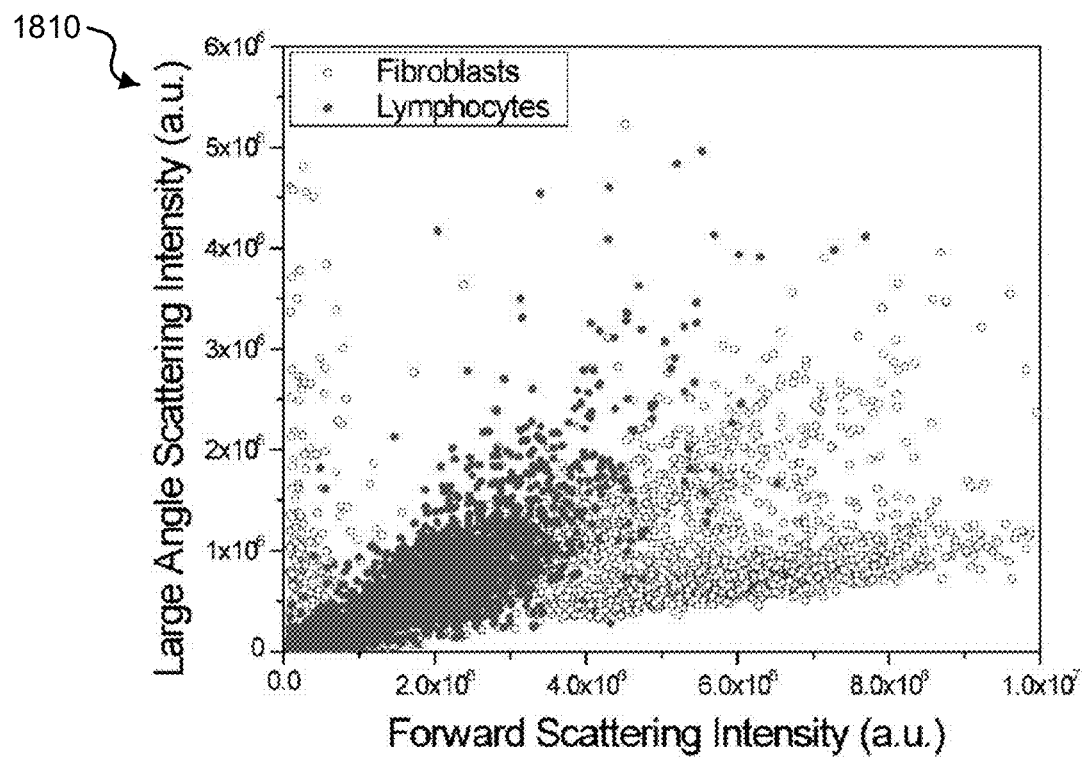
FIG. 18A shows an exemplary scatter plot of the distribution of FS and LAS signals of lymphocytes and fibroblasts superimposed.

Exemplary implementations of the present SVM techniques were performed to demonstrate the flexibilities of using the disclosed optical-coding microfluidic technology to analyze biological cells, e.g., in which fibroblasts and lymphocytes were employed for the measurements. For example, the cultured fibroblasts with the average diameter of 15 µm and lymphocytes with average diameter of 8 µm were introduced into an exemplary optical space-time coding microfluidic device of the present technology at the flow rate of 35 µL/min, respectively. For example, after signal processing and extracting the events for each cell type, the scatter plots for FS and LAS signals of lymphocytes and fibroblasts were superimposed on a plot 1810, as shown in FIG. 18A. For comparison, implementation using a commercial Accuri C6 flow cytometery system was conducted. In this example, with just two dimensions comprised of FS and LAS, the accuracy of using the exemplary microfluidic device of the disclosed technology was shown to be 61.05%. Also, for example, the accuracy from Accuri C6 was shown to be 74.18% using the same two FS and LAS parameters. Based on these exemplary results, it was observed that due to undistinguished populations for two cell types, two-dimensional analysis was not able to generate an appropriate hyperplane for classifying.

Figure 18B:
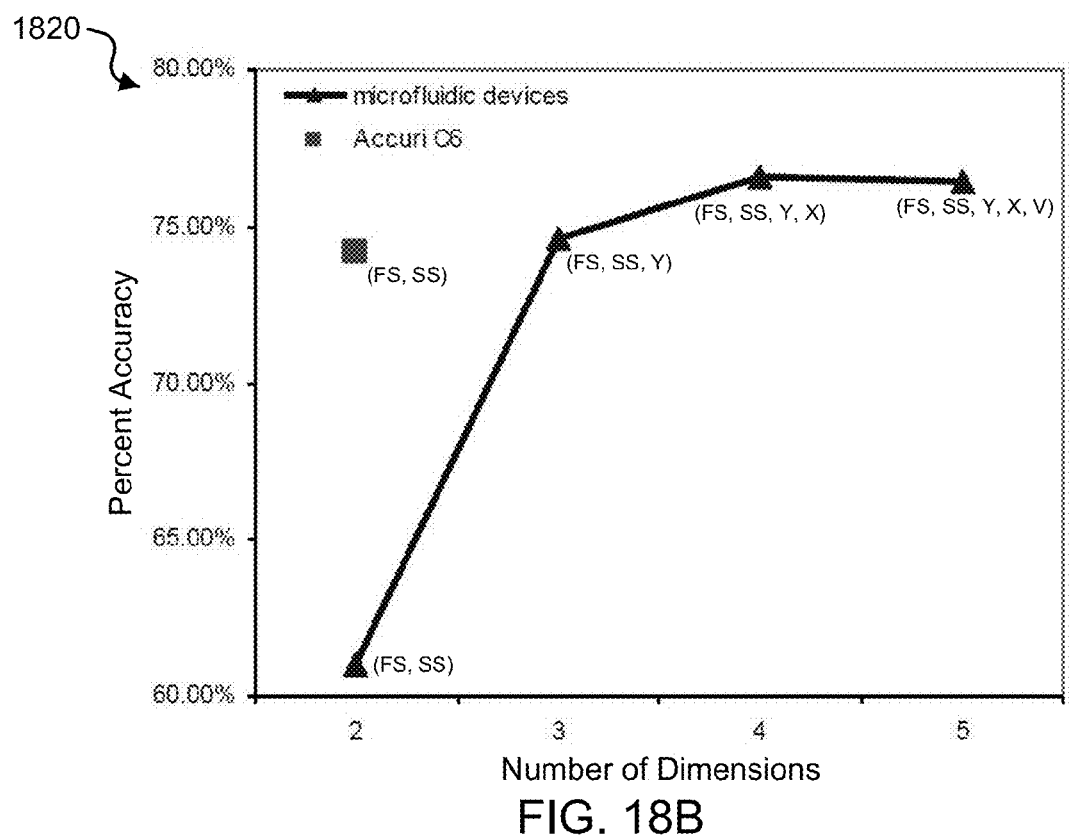
FIG. 18B shows a plot characterizing the accuracy from an exemplary implementation of an exemplary SVM analysis of the lymphocytes and fibroblasts.

Therefore, expanding two dimensions into a higher dimensional feature space can be beneficial for the classification of cells using the disclosed microfluidic technology. For example, the size difference between lymphocytes and fibroblasts allows lift force to influence the distribution of position along x-axis within the microchannel. For example, one can expect fibroblasts have larger size so that fibroblasts would migrate toward the center of the microchannel. Thus, for example, it was calculated that the average positions for lymphocytes and fibroblasts are 32.78 µm and 37.11 µm with the deviation of 15.38 µm and 9.39 µm, respectively, suggesting the distribution of fibroblasts is more close to central channel as well as more concentrated. Although the distributions of x-axis position of two cell types are partially overlapping, this position difference can enhance the accuracy, e.g., which was shown to be 74.63% in this example (FIG. 18B). FIG. 18B shows a plot 1820 of the accuracy from SVM analysis using an exemplary microfluidic device of the disclosed technology and a comparative flow cytometer system versus dimensions applied, which shows the accuracy of classification was improved by higher-dimensional SVM analysis. For example, as shown in FIG. 18B, by adding a fourth dimension, e.g., the position along y-axis, can increase the accuracy further to 76.60%. For example, when a fifth dimension is added, e.g., the velocity of cells, the fifth dimension can be included into SVM analysis to further improve the accuracy. For example, it is because that the position along y-axis is derived from the velocity so the information that could be facilitated for classifying has been evolved from y-position. For example, in the present binary system, the minimal accuracy is 50%; therefore, this exemplary multi-dimensional technique for the cell discrimination has enhanced the accuracy from 61% to 77% that is almost three-fold improvement, e.g., thereby demonstrating that the exemplary microfluidic device can address the application of classifying real biological cells with high performance.

Figure 19A:
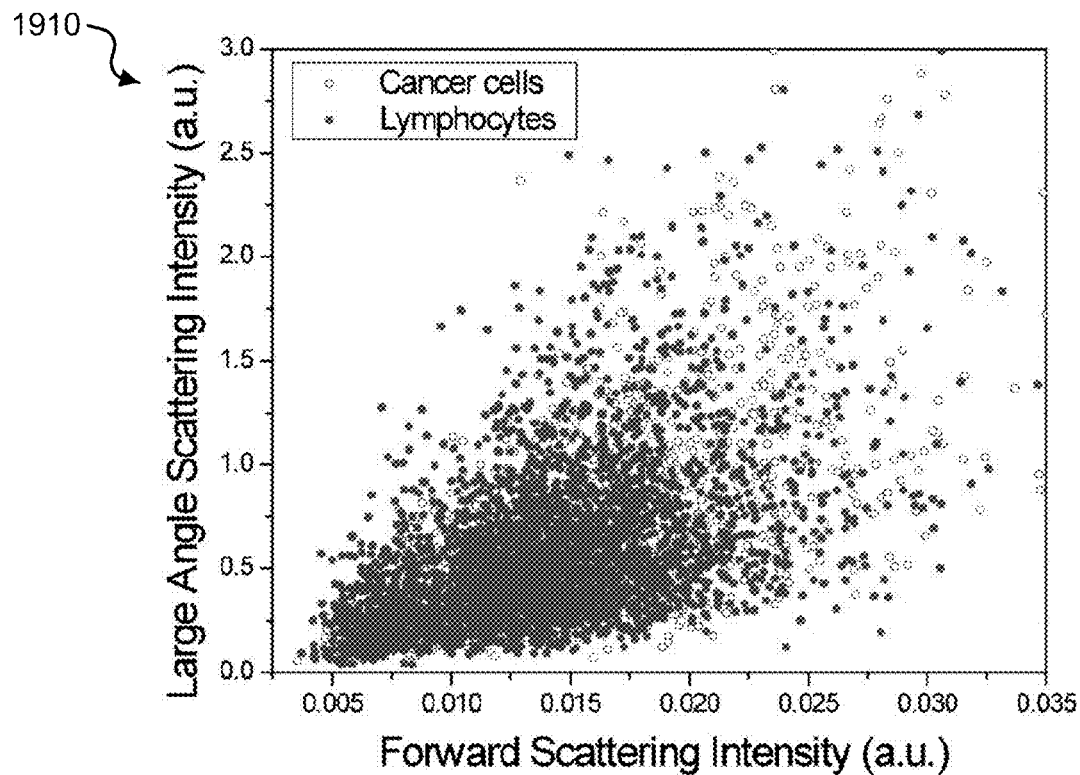
FIG. 19A shows an exemplary scatter plot of the distribution of FS and LAS signals of lymphocytes and cancer cells superimposed.
Figure 19B:
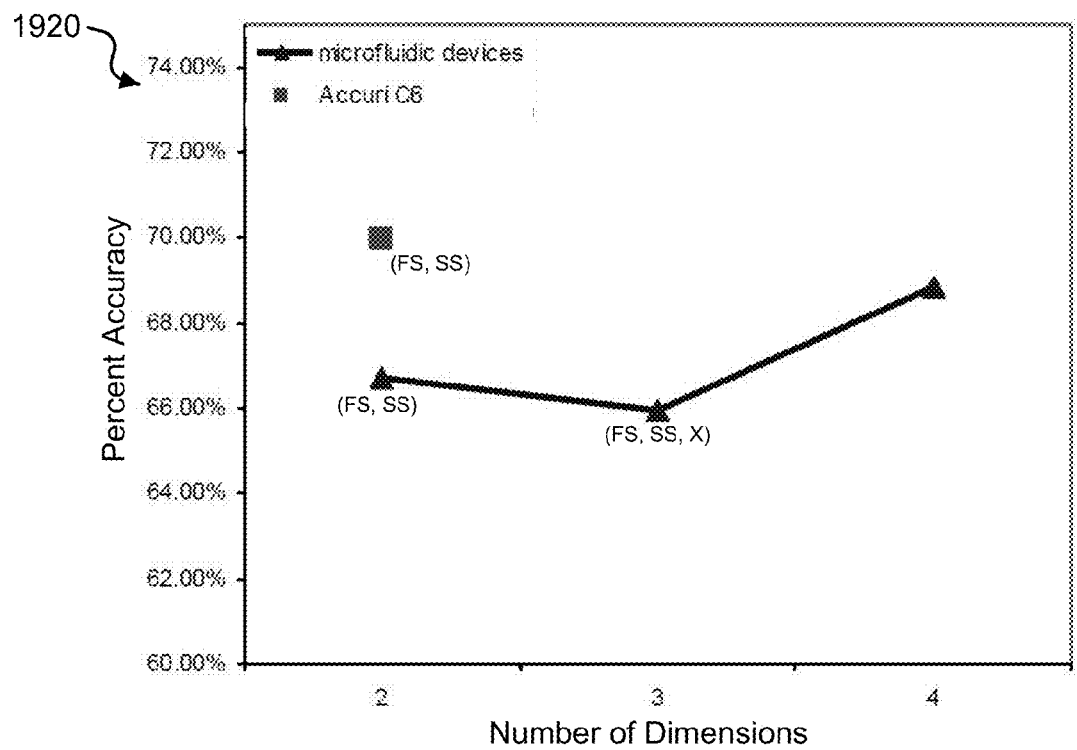
FIG. 19B shows a plot characterizing the accuracy from an exemplary implementation of an exemplary SVM analysis of the lymphocytes and cancer cells.

Exemplary implementations were performed to demonstrate the effectiveness of the present SVM techniques using the disclosed optical-coding microfluidic technology on the clinical application. For example, brain cancer cells were tested to mimic the circulating tumor cells condition. Herein, for the simplicity, a binary cell combination including brain cancer cells and lymphocytes were adopted. The exemplary FS and LAS signals of cultured brain cancer cells with ~30 µm in diameter and the same lymphocytes as described above were recorded at the flow rate of 50 µL/min, respectively. FIG. 19A shows a plot 1910 of the superimposed scatter plot of lymphocytes and cancer cells. For comparison, implementation using a commercial Accuri C6 flow cytometery system was conducted using these two types of cells. In this example, it was shown that two types of cells mostly overlap to each other, resulting in the accuracy of two-dimensional analysis is 66.69% (as shown in FIG. 19B). FIG. 19B shows a plot 1920 of the accuracy from SVM analysis using an exemplary microfluidic device of the disclosed technology and a comparative flow cytometer system versus dimensions applied, which shows the accuracy of classification was improved by higher-dimensional SVM analysis. For example, after adding a third dimensional parameter (e.g., x-position) into SVM analysis, the accuracy was reduced to 65.95%. This exemplary result might be because the total events of lymphocytes outcome the events of cancer cells; e.g., additionally, the average positions of lymphocytes and cancer cells are 51.76 µm and 49.11 µm with the standard deviation of 15.85 µm and 14.98 µm, respectively, indicating that the position distribution of lymphocytes overwhelms the cancer cells along the direction x-axis. On the other hand, for example, when the y-position was incorporated into the exemplary SVM analysis, the accuracy was improved to 68.83%. It was found that although the position difference along y-axis between two kinds of cells was 0.52 µm, but the standard deviation of cancer cells was 1.82 µm (e.g., that is almost half value of lymphocytes, 3.53 µm). For example, the smaller deviation of the y-position of cancer cells might be attributed to the deformability of cells. This small standard deviation allowed the exemplary SVM analysis to create a separating hyperplane, e.g., increasing accuracy to the level comparable to the accuracy of Accuri C6 (e.g., shown to be 69.97%). The present SVM techniques exhibited a practical method that can be implemented to provide accurate cell discrimination using the disclosed optical space-time coding microfluidic technology (e.g., which can be used in clinical uses with using low-cost lab-on-a-chip devices). For example, the exemplary implementations of the present SVM techniques with the exemplary microfluidic devices were shown to be comparable with conventional machines for classifying biological samples.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, e.g., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non volatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A microfluidic device for optical detection of particles, comprising:
   a substrate;
   a microfluidic channel formed on the substrate and structured to carry a fluid sample containing particles, the microfluidic channel structured to transmit a probe light; and
   a mask formed on one side of the microfluidic channel and structured to include a pattern of openings along the microfluidic channel, wherein at least two of the openings have varying longitudinal and transverse dimensions with respect to a fluid flow direction across the microfluidic channel, and wherein the pattern of openings encodes a waveform on the probe light that transmits through the microfluidic channel to allow optical detection of a position of a particle in at least two dimensions in the microfluidic channel.

2. The device of claim 1, further comprising:
   a light source that generates the probe light through the pattern of openings to illuminate the fluid sample, wherein each particle scatters the light beam to produce an optical scattering signal at each position that the particle flows along the pattern of openings of the microfluidic channel; and
   an optical detector arranged in a location relative to the pattern of openings to receive the optical scattering signal and produce a scattering signal waveform including signal peaks corresponding to the openings of the pattern of openings, respectively.

3. The device of claim 2, further comprising:
   a processing unit communicatively coupled to the optical detector that processes the scattering signal waveform to determine the position of the particle.

4. The device of claim 3, wherein the processing unit determines the position of the particle based on the width of at least two signal peaks of the scattering signal waveform corresponding to the at least two openings of the pattern of openings with unequal widths.

5. The device of claim 3, wherein the processing unit determines a velocity of the particle based on the position of the particle.

6. The device of claim 3, wherein the processing unit determines a multidimensional positional distribution of the particle in the microfluidic channel.

7. The device of claim 3, wherein the processing unit determines fluid dynamic properties of the particle in the microfluidic channel including at least one of inertial focusing, Dean's flow, or flow confinement.

8. The device of claim 2, wherein the location of the optical detector is between 5 to 10 degrees relative to the pattern of openings to receive a forward scattering (FS) signal.

9. The device of claim 2, wherein the location of the optical detector is between 45 to 60 degrees relative to the pattern of openings to receive a large angle scattering (LAS) signal.

10. The device of claim 2, wherein the location of the optical detector is substantially 90 degrees relative to the pattern of openings to receive a side scattering (SS) signal.

11. The device of claim 2, wherein the light source includes at least one of a semiconductor laser diode or a mercury arc lamp.

12. The device of claim 2, wherein the optical detector includes a silicon PIN photodiode.

13. The device of claim 1, wherein the pattern of openings comprises four trapezoidal shapes.

14. The device of claim 1, wherein the device determines at least one of size, shape, and granularity of the particles of the fluid sample.

15. The device of claim 1, wherein the fluid sample is blood sample.

16. The device of claim 15, wherein the blood sample prepared without the use of centrifugation, addition of anti-coagulation agents, antibody labeling, filtering, and pipetting.

17. The device of claim 16, wherein the processing unit determines the quantity of neutrophil cells from among the other cells of the blood sample based on the size distribution of the cells of the blood sample.

18. A method of determining a position of particle in a microfluidic channel, comprising:
   transferring a fluid sample containing particles through a microfluidic channel having an pattern of apertures spatially arranged on a surface of the channel, wherein at least two of the apertures have varying longitudinal and transverse dimensions with respect to a fluid flow direction across the microfluidic channel;

transmitting a light beam through the pattern of apertures to illuminate the fluid sample, wherein each particle scatters the light beam to produce an optical scattering signal at each position along the pattern of apertures;

detecting the optical scattering signal with an optical detector configured at a scattering angle formed between the optical detector and the pattern of apertures, wherein the detected optical scattering signal produces a scattering signal waveform; and processing the scattering signal waveform to determine the position of the particle in at least two dimensions.

19. The method of claim 18, further comprising determining the velocity of the particle based on the determined position of the particle.

20. The method of claim 18, further comprising determining a multidimensional positional distribution of the particle in the microfluidic channel.

21. The method of claim 18, further comprising determining fluid dynamic properties of the particle in the microfluidic channel including at least one of inertial focusing, Dean's flow, or flow confinement.

22. The method of claim 18, further comprising determining at least one of size, shape, and granularity of the particles of the fluid sample.

23. The method of claim 22, wherein the fluid sample is blood sample.

24. The method of claim 23, further comprising quantifying the number of neutrophil cells from among the other cells of the blood sample based on a distribution of cell size.

25. A microfluidic device, comprising:

a microfluidic channel structured to carry a fluid sample containing particles along a fluid flow direction from an inlet region to an outlet region, the microfluidic channel including a pattern of openings spatially arranged on a surface of the channel, wherein at least two openings of the pattern of openings have unequal widths in a longitudinal dimension and a transverse dimension along the fluid flow direction;

a light source that generates a light beam through the pattern of openings to illuminate the fluid sample, wherein each particle scatters the light beam to produce an optical scattering signal at each position that the particle flows along the pattern of openings of the microfluidic channel;

an optical detector arranged in a location relative to the pattern of openings to receive the optical scattering signal and produce a scattering signal waveform, the waveform including a signal peak corresponding to each opening of the pattern of openings; and a data processing and storage unit communicatively coupled to the optical detector, the data processing and storage unit to convert the scattering signal waveform from an analog signal format to a digital signal representation and to store the digital signal representation in a data storage.

26. The microfluidic device of claim 25, further comprising an input/output (I/O) unit communicatively coupled to the data processing and storage unit to interface with an external computer system that can retrieve the digital signal representation from the data storage to the external computer system.

27. The microfluidic device of claim 26, wherein the external computer system includes at least one of a personal computer, tablet, or smartphone device.

\* \* \* \* \*